(12) United States Patent
Trinh et al.

(10) Patent No.: US 9,410,194 B2
(45) Date of Patent: Aug. 9, 2016

(54) COMPOSITIONS, KITS AND METHODS FOR SYNTHESIS AND/OR DETECTION OF NUCLEIC ACIDS

(75) Inventors: Christopher Trinh, San Jose, CA (US); Tom Xu, Castro Valley, CA (US); Yating Shi, San Leadro, CA (US); Ferrier Le, San Jose, CA (US); Claire Marjoribanks, Campbell, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 943 days.

(21) Appl. No.: 13/165,571

(22) Filed: Jun. 21, 2011

(65) Prior Publication Data

US 2012/0244527 A1 Sep. 27, 2012

Related U.S. Application Data

(60) Provisional application No. 61/357,031, filed on Jun. 21, 2010.

(51) Int. Cl.
*C12Q 1/68* (2006.01)
*C12P 19/34* (2006.01)

(52) U.S. Cl.
CPC ..................................... *C12Q 1/686* (2013.01)

(58) Field of Classification Search
CPC ....................................................... C12Q 1/686
See application file for complete search history.

(56) References Cited

U.S. PATENT DOCUMENTS

| | | | |
|---|---|---|---|
| 6,558,929 B2 | 5/2003 | Thum et al. | |
| 2003/0082577 A1 | 5/2003 | Cockerill et al. | |
| 2003/0215811 A1 | 11/2003 | Schaefer et al. | |
| 2005/0129581 A1* | 6/2005 | McBride | B01L 3/5027 422/503 |
| 2008/0286772 A1 | 11/2008 | Chang et al. | |
| 2012/0156750 A1* | 6/2012 | Battrell | C12Q 1/6806 435/188 |

FOREIGN PATENT DOCUMENTS

| | | |
|---|---|---|
| EP | 0989192 | 3/2000 |
| EP | 1072678 A1 | 1/2001 |
| WO | 2008/155524 A1 | 12/2008 |
| WO | 2009/016652 A1 | 2/2009 |
| WO | 2011/163120 A1 | 12/2011 |
| WO | 2011/163249 A2 | 12/2011 |

OTHER PUBLICATIONS

Chaves et al., "Noninvasive genetic sampling of endangered muriqui (Primates, Atelidae): Efficiency of fecal DNA extraction," Genetic and Molecular Biology, 2006, vol. 29, No. 4, pp. 750-754.*
Kramer et al., "Enzymatic Amplification of DNA of PCR: Standard Procedures and Optimization," Current Protocols in Toxicology, 2000, Suppl. 3, A.3.C1-A.3C.14 (pp. 1-14).*
Yap et al., "Slide PCR: DNA amplification from cell samples on microscopic glass slides," Nucleic Acids Research, 1991, vol. 19, No. 15, p. 4294.*
Kreader et al., "Relief of Amplification Inhibition in PCR with Bovine Serum Albumin or T4 Gene 32 Protein," Applied and Environmental Microbiology, 1996, vol. 62, No. 3, pp. 1102-1106.*
EP Application No. 2582850, Extended European Search Report mailed Nov. 27, 2013, 1-12.
Intl Application No. PCT/US2011/041275; International Preliminary Report on Patentability mailed Dec. 28, 2012, 1-4.
Nagai et al., "Additive Effects of Bovine Serum Albumin, Dithiothreitol, and Glycerol on PCR", *Biochemistry and Molecular Biology International*, vol. 44, No. 1, Jan. 1, 1998, 157-163.
Abu Al-Soud, W. et al., "Effects of Amplification Facilitators on Diagnostic PCR in the Presence of Blood, Feces, and Meat", *Journal of Clinical Microbiology*, Lund Institute of Technology, Lund University, Lund, Sweden., Dec. 2000, 4463-4470.
King, C. et al., "A Quantitative Approach to Detect and Overcome PCR Inhibition in Ancient DNA Extracts", *Biotechniques*, vol. 47, No. 5, 2009, 941-949.
Opel, K. L. et al., "A Study of PCR Inhibition Mechanisms Using Real Time PCR", *J. Forensic Sci.*, vol. 55, No. 1, 2010, 25-33.
PCT/US2011/041275, PCT International Search Report and Written Opinion mailed Feb. 24, 2012.
Chung, D., "The Development of Novel STR Miniplex Primer Sets for the Analysis of Degraded and Compromised DNA Samples" Electronic Thesis or Dissertation, Ohio University, Aug. 30, 2004, pp. 1-217.

* cited by examiner

*Primary Examiner* — Young J Kim

(57) ABSTRACT

A composition comprising a thermostable DNA polymerase; and a PCR inhibitor blocking agent, wherein the PCR inhibitor blocking agent is present in an amount effective to enhance tolerance of an assembled PCR to a PCR inhibitor.

20 Claims, 13 Drawing Sheets

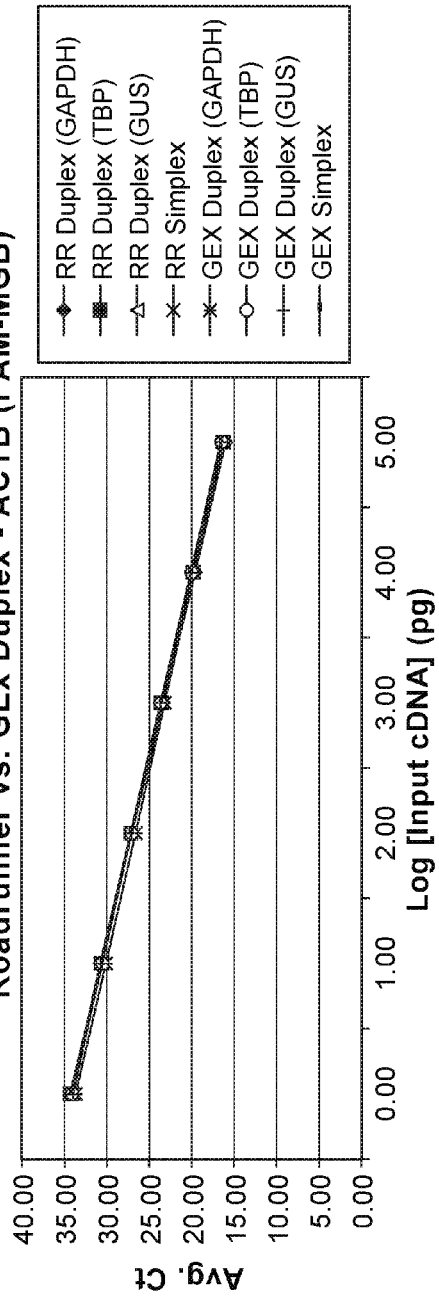
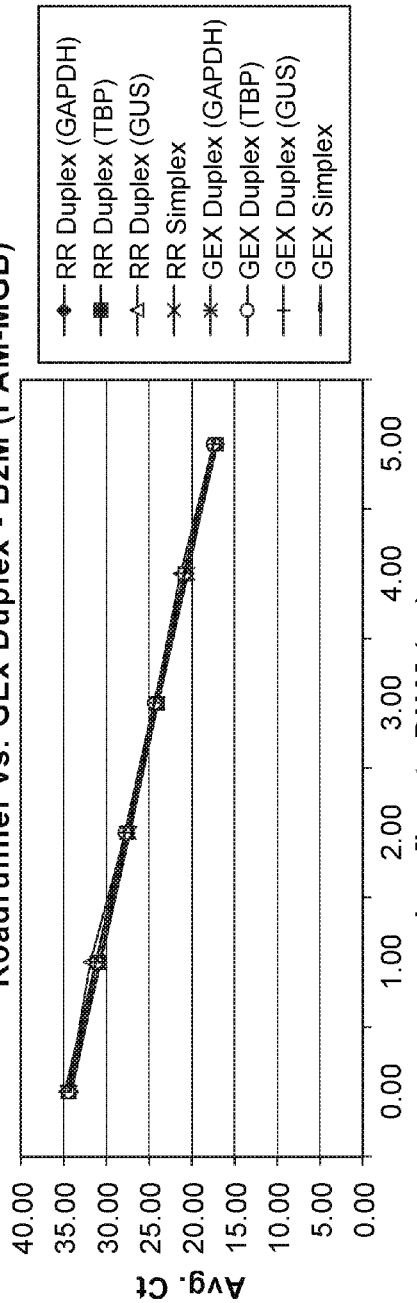

COMPOSITIONS, KITS AND METHODS FOR SYNTHESIS AND/OR DETECTION OF NUCLEIC ACIDS

CROSS REFERENCE TO RELATED APPLICATIONS

This application claims benefit of priority under 35 U.S.C. 119(e) from the U.S. Provisional Application No. 61/357,031 filed 21 Jun. 2010, which is incorporated hereby in its entirety.

BACKGROUND

This disclosure relates to compositions, kits, and methods for the synthesis and/or detection of nucleic acids.

For many medical, diagnostic, and forensic applications, amplification of a particular DNA sequence is essential to allow its detection in, or isolation from, a sample in which it is present in very low amounts. More recently, in vitro amplification of specific genes has provided powerful and less costly means to facilitate the production of therapeutic proteins by molecular biological techniques, and may have applications in genetic therapy as well.

The polymerase chain reaction (PCR) technique is disclosed in U.S. Pat. Nos. 4,683,202; 4,683,195; 4,800,159; and 4,965,188. The PCR method is also described in Saiki et al., 1985, Science 230:1350. In its simplest form, PCR is an in vitro method for the enzymatic synthesis of specific DNA sequences using two oligonucleotide primers that hybridize to opposite strands and flank the region of interest in the target DNA. A repetitive series of reaction steps involving template denaturation, primer annealing, and the extension of the annealed primers by DNA polymerase results in the exponential accumulation of a specific fragment whose termini are defined by the 5' ends of the primers. PCR is capable of producing a selective enrichment of a specific DNA sequence by a factor of $10^9$.

Commercially available PCR master mixes improve the efficiency and reduce the errors associated with the assembly of large number of PCR reactions required for high-throughput analysis. These master mixes contain a combination of reagents that will be common to all PCR reactions. For example, the master mix may contain a buffer, a salt such as $MgCl_2$, deoxynucleoside triphosphates (dNTPs), and a thermostable DNA polymerase. Each well would contain the common master mix and a specific target nucleic acid and primer pair. Typically, master mixes are manufactured and distributed as concentrated solutions or lyophilized powders which are subsequently diluted or dissolved when final reactions are assembled.

For accurate analysis, PCR master mixes should provide reliable, robust, and reproducible PCR results. Further, PCR master mixes should allow for detection of low copy number target nucleic acids. The PCR master mix should also allow for fast PCR reaction cycles to allow rapid screening of nucleic acids (e.g., DNAs and cDNAs). In addition, the PCR master mix should also be stable on the bench top at ambient or room temperature so that the PCR reactions need not be amplified immediately after assembly.

Sources for nucleic acid samples include, but are not limited to, for example clothing, soil, paper, metal surfaces, air, water, plant parts, as well as human and/or animal skin, hair, blood, serum, feces, milk, saliva, urine, and/or other secretory fluids. These sources may also contain compounds that inhibit PCR amplification.

Accordingly, there is a need to identify agents that block or reduce the inhibition of PCR amplification by components found in sources for nucleic acid samples.

SUMMARY

Disclosed herein are compositions, kits, and methods for the synthesis and/or detection of nucleic acids by polymerase chain reaction, comprising a DNA polymerase and a PCR inhibitor blocking agent. The PCR inhibitor blocking agent relieves inhibition of PCR caused by a variety of compounds often found in samples containing nucleic acids that are analyzed by PCR. The compositions, kits, and methods disclosed herein ensure sensitive and reliable PCR results over a wide range of target nucleic acid concentrations. The composition also allows for rapid results in fast PCR thermal cyclers. The composition also provides assembled PCR reactions that may be stable for up to 72 hours or more at room temperature.

Disclosed herein are compositions comprising a thermostable DNA polymerase; and a PCR inhibitor blocking agent, wherein the PCR inhibitor blocking agent is present in an amount effective to enhance tolerance of an assembled PCR to a PCR inhibitor.

Also disclosed herein is a kit comprising a composition comprising a thermostable DNA polymerase and a PCR inhibitor blocking agent, wherein the PCR inhibitor blocking agent is present in an amount effective to enhance tolerance of an assembled PCR to a PCR inhibitor.

Further disclosed herein is a kit comprising a composition comprising a thermostable DNA polymerase and a PCR inhibitor blocking agent, wherein the PCR inhibitor blocking agent is present in an amount effective to enhance tolerance of an assembled PCR to a PCR inhibitor, a primer, and a labeled probe.

Further disclosed herein is a method for nucleic acid synthesis comprising mixing a composition comprising a thermostable DNA polymerase and a PCR inhibitor blocking agent, wherein the PCR inhibitor blocking agent is present in an amount effective to enhance tolerance of an assembled PCR to a PCR inhibitor, with a nucleic acid sample and a primer; and synthesizing a nucleic acid using the nucleic acid sample as a template. In some embodiments, synthesis can occur up to 72 hours following the mixing of the composition with a nucleic acid sample and a primer or primers.

Further disclosed herein is a method for the assembly of a polymerase chain reaction (PCR) comprising adding a composition comprising a thermostable DNA polymerase and a PCR inhibitor blocking agent, wherein the PCR inhibitor blocking agent is present in an amount effective to enhance tolerance of an assembled PCR to a PCR inhibitor, to a reaction vessel; and adding a nucleic acid sample and a primer to the reaction vessel.

Further disclosed herein is a method for amplifying a nucleic acid by polymerase chain reaction (PCR) comprising adding a composition comprising a thermostable DNA polymerase and a PCR inhibitor blocking agent, wherein the PCR inhibitor blocking agent is present in an amount effective to enhance tolerance of an assembled PCR, to a PCR inhibitor to a reaction vessel; adding a nucleic acid sample and a primer to the reaction vessel; and performing PCR on the nucleic acid sample.

Further disclosed herein is a method for detecting a nucleic acid by polymerase chain reaction (PCR) comprising adding a composition comprising a thermostable DNA polymerase and a PCR inhibitor blocking agent, wherein the PCR inhibitor blocking agent is present in an amount effective to enhance tolerance of an assembled PCR to a PCR inhibitor, to a reaction vessel; adding a nucleic acid sample and a primer to the reaction vessel; performing PCR on the nucleic acid sample; and detecting amplified target.

Further disclosed herein is a method for blocking inhibition of a polymerase chain reaction (PCR) by PCR inhibitors comprising adding a composition comprising a thermostable DNA polymerase and a PCR inhibitor blocking agent, wherein the PCR inhibitor blocking agent is present in an amount effective to enhance tolerance of an assembled PCR to a PCR inhibitor, to a reaction vessel, wherein the composition blocks inhibition of PCR by PCR inhibitors; adding a nucleic acid sample and a primer to the reaction vessel; and performing PCR on the nucleic acid sample.

Further disclosed herein is a method for decreasing the run time of a polymerase chain reaction (PCR) by PCR inhibitors comprising adding a composition comprising a thermostable DNA polymerase and a PCR inhibitor blocking agent, wherein the PCR inhibitor blocking agent is present in an amount effective to enhance tolerance of an assembled PCR to a PCR inhibitor, to a reaction vessel, wherein the composition decreases the run time of a PCR; adding a nucleic acid sample and a primer to the reaction vessel; and performing PCR on the nucleic acid sample.

The above described and other features are exemplified by the following figures and detailed description.

BRIEF DESCRIPTION OF THE DRAWINGS

(FIG. 3B).

FIGS. 10A-10B presents graphs showing results in simplex and duplex amplification reactions under fast thermal cycling conditions.

DETAILED DESCRIPTION

Figure 1:
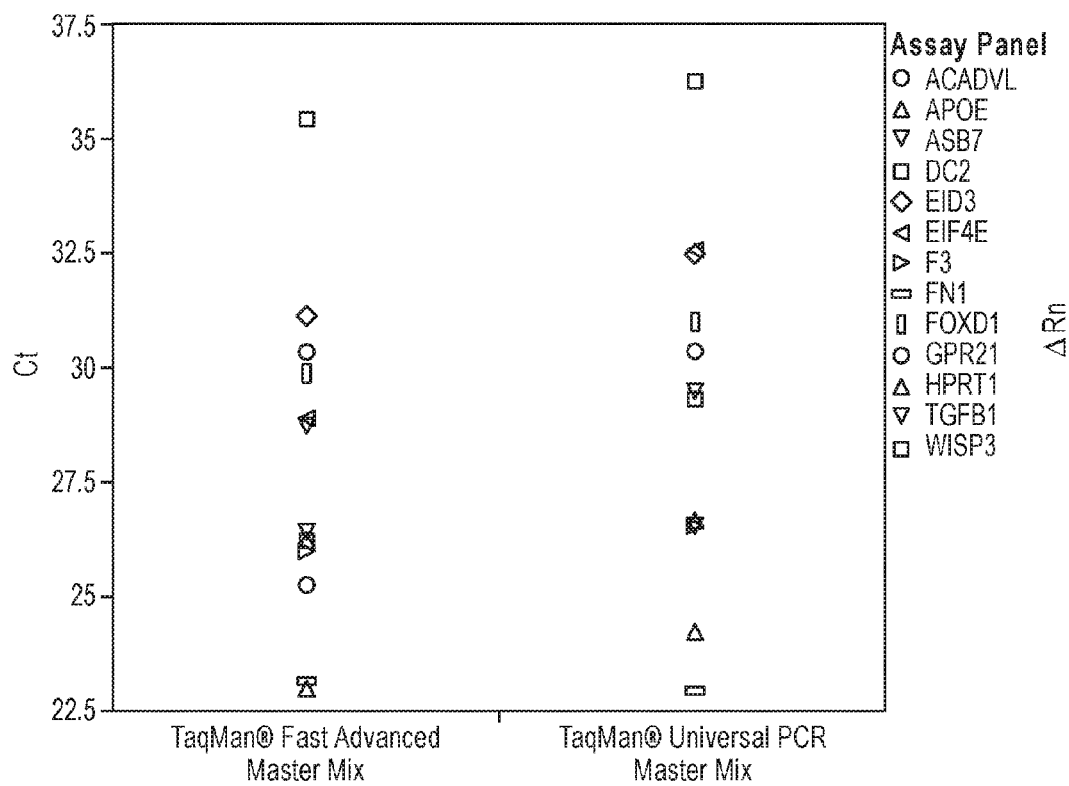
FIG. 1 shows a plot comparing threshold cycle (Ct) for a panel of 13 TAQMAN® Gene Expression assays using an embodiment of the compositions disclosed herein at a 2× concentration and a commercial composition, TAQMAN® Universal PCR Master Mix.

The present disclosure relates generally to ready-to-use reagent mixtures, kits, and methods for the detection and/or quantitation of nucleic acids.

Improved compositions with unexpectedly superior properties have been developed. The inventive compositions provide assembled polymerase chain reactions (PCRs) master mix showing superior sensitivity, accuracy, dynamic range, and specificity compared to PCRs assembled with standard reagent mixes when run on standard PCR instrumentation. In some embodiments, the superior sensitivity of PCRs assembled with the compositions disclosed herein permits reduced PCR run times on either FAST or standard PCR instrumentation. Further, in some embodiments, the compositions disclosed herein provide assembled PCRs with unusually long stability at room temperature (e.g., 23-30° C.), up to 72 hours, a feature that is beneficial to the accuracy of results obtained by users of high-throughput liquid handling systems.

In some embodiments, the compositions disclosed herein are useful in a wide range of assays detecting nucleic acids. For example, the compositions can be used in PCR-based assays for detecting gene expression, microRNA (miRNA) expression, or genotyping.

Kits comprising the compositions are also disclosed, as are methods of using the compositions and kits.

In one embodiment, the composition comprises a thermostable DNA polymerase and a PCR inhibitor blocking agent, wherein the PCR inhibitor blocking agent is present in an amount effective to enhance tolerance of an assembled PCR to a PCR inhibitor. In an embodiment, the PCR inhibitor blocking agent is a protein. Suitable proteins include albumin and gelatin. In some embodiments, the PCR inhibitor blocking agent is selected from serum albumin, fish gelatin, or a combination of the foregoing, wherein the component is present in an amount effective to enhance tolerance of an assembled PCR for PCR inhibitors. The serum albumin can be from any animal, e.g., bovine serum albumin (BSA), human serum albumin (HSA). In an embodiment, the composition comprises albumin at a concentration such that its concentration in an assembled PCR (e.g., a working solution) is about 0.05 mg/mL to about 0.8 mg/mL, about 0.1 mg/mL to about 0.6 mg/mL, and more specifically about 0.2 mg/mL to about 0.4 mg/mL, gelatin at a concentration such that its concentration in an assembled PCR is about 0.05% (w/v) to about 0.8% (w/v), and more specifically about 0.2% (w/v) to about 0.4% (w/v), or a combination of the foregoing. In another embodiment, the PCR inhibitor blocking agent can be albumin at about 0.3 mg/mL and gelatin at a concentration of about 0.3% (w/v). In one embodiment, the albumin is BSA, and the gelatin is fish gelatin.

In some embodiments, thermostable DNA polymerases as used herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°-100° C. under conditions such as is typically required for PCR amplification.

In some embodiments, the composition can further comprise additional components, e.g. glycerol, bovine gelatin, NaN$_3$, a buffer, salts, dNTPs, surfactants, and/or generally any cationic, anionic, Zwitterionic, and/or nonionic detergent, a reagent for hotstart PCR, a passive reference control to minimize sample-to-sample and/or well-to-well variations in quantitative real-time DNA-detection assays, and/or uracil DNA glycosylase. The composition may further comprise crowding agents such as Ficoll 70, glycogen, and polyethylene glycol (PEG).

In some embodiments, glycerol can be present in the composition at a concentration such that its concentration in the assembled PCR is about 6 to about 11% (w/v), specifically about 8.5% (w/v). Bovine gelatin can be present in the composition at a concentration such that its concentration in the assembled PCR is about 0.3 to about 0.7% (w/v), specifically about 0.5% (w/v). NaN$_3$ can be present in the composition at a concentration such that its concentration in the assembled PCR is about 0.007 to about 0.013% (w/v), specifically about 0.01% (w/v).

The composition may comprise buffer agents and/or salt solutions to provide appropriate pH and ionic conditions to maintain stability of the DNA polymerase enzyme. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about 3 days at a temperature of about room temperature (e.g., about 20° C. to about 25° C.), about one week at a temperature of about 4° C., about two to six months at a temperature of about −20° C., and about six months or longer at a temperature of about −80° C. Examples of such buffering agents can include, for example, TRIS, TRICINE, BIS-TRICINE, HEPES, MOPS, TES TAPS, PIPES, and CAPS. Examples of such salt solutions can include, for example, potassium chloride, potassium acetate, potassium sulfate, ammonium sulfate, ammonium chloride, ammonium acetate, magnesium chloride, magnesium acetate, magnesium sulfate manganese chloride, manganese acetate, manganese sulfate, sodium chloride, sodium acetate, lithium chloride and lithium acetate. It is to be understood that a wide variety of buffers and salt solutions are known in the art that, including those not specifically disclosed herein.

In another embodiment, the compositions can be provided as a concentrated stock. As used herein, the term "concentrated stock" means at a concentration that requires further dilution in order to achieve optimal concentration for use in a solution to perform a particular function (such as PCR amplification). For example, compositions may be stock solutions of about 2×, about 3×, about 4×, about 5×, about 6×, about 10×, and so on. In some preferred embodiments, the compositions may require greater than 2×, greater than 3×, greater than 4×, greater than 5×, greater than 6×, greater than 10×, and so on, dilution to be at working, or optimal, concentration for use in nucleic acid synthesis methods.

dNTPs can be provided in the composition. Concentrations of each dNTP included in the composition should be such that a concentration of about 0.15 mM to about 0.65 mM of the dNTP is achieved in the assembled PCR. The dNTPs included can be dATP, dCTP, dGTP, dTTP, or dUTP. The concentration of the individual dNTPs need not be identical. In an embodiment, dATP, dCTP, dGTP are present in the composition at a concentration such that each has a concentration in the assembled PCR is about 0.15 to about 0.35 mM, specifically about 0.25 mM, and dUTP is present in the composition at a concentration such that its concentration in the assembled PCR is about 0.35 to about 0.65 mM, specifically about 0.5 mM The nonionic detergent can be, for example, TRITON X-1000, Nonidet P-40 (NP-40), TWEEN 20 or Brij 35. The nonionic detergent can be present in the composition at a concentration such that its concentration in the assembled PCR is about 0.007 to about 0.013% (w/v), specifically about 0.01% (w/v). In some embodiments, TWEEN-20 is present in the composition at a concentration such that its concentration in the assembled PCR is about 0.007% (w/v).

The reagent for hotstart PCR can be an antibody, an aptamer, a hairpin primer, or a sequestration wax bead. Wax beads for hotstart PCR are commercially available, e.g., AmpliWax® PCR Gem 100 and AmpliWax® PCR Gem 50 (Applied Biosystems). Selection of a suitable aptamer can be performed by a method known in the art or a commercially available aptamer can be used. Similarly, selection of a suitable hairpin primer can be performed by a method known in the art or a commercially available primer can be used. Antibodies for hotstart PCR can be generated or selected by a method known in the art. Alternatively, a commercially available antibody can be used, for example, the TaqStart Antibody (Clontech) which is effective with any Taq-derived DNA polymerase, including native, recombinant, and N-terminal deletion mutants. An appropriate concentration of the reagent for hotstart PCR in the assembled PCR can be determined by a method known in the art or, for a commercial product, suggested by the manufacturer.

The passive reference control to minimize sample-to-sample and/or well-to-well variations in quantitative real-time nucleic acid-detection assays can be included at a concentration allowing its use as detectable control. In an embodiment, a reference chromophore, specifically a fluorophore, is included as the passive reference control. In an embodiment, the reference chromophore is the dye ROX (Invitrogen). ROX can be included in the composition at a concentration such that its concentration in the final assembled PCR is about 40 to about 80 nM, specifically about 60 nM.

Uracil DNA glycosylase (UNG) can be included in the composition. The enzyme is commercially available from a number of commercial sources, for example Invitrogen, Enzymatics, New England Biolabs, Genscript, or USB. UNG can be included in the composition at a concentration such that its concentration in the final assembled PCR is about 0.005 to about 0.015 U/μL, specifically about 0.01 U/μL.

In an embodiment, the composition comprises a thermostable DNA polymerase, a combination of PCR inhibitor blocking agents, a buffered salt solution, a hot start component, dNTPs, glycerol, a nonionic detergent, and a passive reference dye. The components may be substituted or modified.

In some embodiments, the disclosed compositions are stable when stored at about −20° C. for at least 5.5 months.

The composition can be packaged in a suitable container capable of holding the composition and which will not significantly interact with components of the composition. The container can be one designed to permit easy dispensing of the dosage form by individuals or by a liquid handling instrument.

The containers of composition can be further packaged into multi-pack units.

Also disclosed herein are kits comprising the compositions. The kits can further comprise reagents used in one or more assays to synthesize, detect or quantify nucleic acids.

In an embodiment, the kit can further comprise in addition to the composition a primer pair specific for PCR amplification of a DNA target, and a probe specific for the DNA target. For example, the probe can be a TAQMAN® probe, a HydrolEasy™ probe, a minor groove binding (MGB) probe, a locked nucleic acid (LNA) probe, or a cycling probe technology (CPT) probe.

In another embodiment, the kit can further comprise a control nucleic acid sample, and a primer pair specific for PCR amplification of a DNA target on the control nucleic acid sample. A probe for detecting the amplification can also be included in the kit.

Components of the kit other than the composition may be provided in individual containers or in a single container, as appropriate. Instructions and protocols for using the kit advantageously can be provided.

The disclosed compositions and kits can be used in a variety of PCR-based assays to detect or quantify nucleic acid. For example, the compositions can be used in gene expression assays (e.g., TAQMAN® Gene Expression Assays), miRNA assays (e.g., TAQMAN® MicroRNA Assays), genotyping assays (e.g., TAQMAN® Drug Metabolism Genotyping Assays or TAQMAN® SNP Genotyping Assays), or RNA quantitation assays (e.g., two-step reverse transcription-polymerase chain reaction assays), and TAQMAN® Low Density Array Assays.

Also disclosed herein are methods of using the reagent concentrations and kits.

In an embodiment a method for the assembly of a polymerase chain reaction (PCR) comprises adding a composition comprising a thermostable DNA polymerase and a PCR inhibitor blocking agent, wherein the PCR inhibitor blocking agent is present in an amount effective to enhance tolerance of an assembled PCR to a PCR inhibitor to a reaction vessel; and adding a nucleic acid sample and a primer to the reaction vessel.

Examples of reaction vessels include microcentrifuge tubes, a well in a wellplate, a capillary tube, or a microfluidic chip.

In an embodiment, a method for amplifying a nucleic acid by polymerase chain reaction (PCR) comprises adding a composition comprising a thermostable DNA polymerase and a PCR inhibitor blocking agent, wherein the PCR inhibitor blocking agent is present in an amount effective to enhance tolerance of an assembled PCR to a PCR inhibitor to a reaction vessel; adding a nucleic acid sample and a primer to the reaction vessel; and performing PCR on the nucleic acid sample, wherein the PCR occurs up to 72 hours following the addition of the composition, nucleic acid sample, and primer to the reaction vessel.

In some embodiments, the methods for amplifying a target nucleic acid can be multiplex PCR amplifications in which multiple targets are simultaneously amplified. The number of targets amplified can be up to 10 targets, specifically up to 6 targets, more specifically up to three targets, yet more specifically two targets. In an embodiment, one of the multiplexed targets is an endogenous or an exogenous internal positive control for amplification.

In general, PCR thermal cycling includes an initial denaturing step at high temperature, followed by a repetitive series of temperature cycles designed to allow template denaturation, primer annealing, and extension of the annealed primers by the polymerase. Generally, the samples are heated initially for about 2 to 10 minutes at a temperature of about 95° C. to denature the double stranded DNA sample. Then, in the beginning of each cycle, the samples are denatured for about 10 to 60 seconds, depending on the samples and the type of instrument used. After denaturing, the primers are allowed to anneal to the target DNA at a lower temperature, from about 40° C. to about 60° C. for about 20 to 60 seconds. Extension of the primers by the polymerase is often carried out at a temperature ranging from about 60° C. to about 72° C. The amount of time used for extension will depend on the size of the amplicon and the type of enzymes used for amplification and is readily determined by routine experimentation. Additionally, the annealing step can be combined with the extension step, resulting in a two step cycling. Thermal cycling may also include additional temperature shifts in PCR assays. The number of cycles used in the assay depends on many factors, including the primers used, the amount of sample DNA present, and the thermal cycling conditions. The number of cycles to be used in any assay may be readily determined by one skilled in the art using routine experimentation. Optionally, a final extension step may be added after the completion of thermal cycling to ensure synthesis of all amplification products.

In one embodiment, exemplary thermal cycling conditions for PCR amplifications using the compositions disclosed herein are as follows:
  UNG Step (Optional): 50° C., 2 min
  Activation: 95° C., 20 sec
  (Denaturation: 95-97° C./1-3 sec)
  (Extension: 60-62° C./20-30 sec)×40 cycles In one embodiment, when the composition disclosed here is used for the TAQMAN® Low Density Array (TLDA) platform, an activation of 92° C. for 10 minutes is recommended.

PCR with the disclosed composition can be performed on "standard" PCR instrumentation, e.g., Applied Biosystems 7900HT, 7500, and 7300 standard PCR systems, or on "Fast" PCR instrumentation, e.g., Applied Biosystems StepOne, StepOne Plus, 7500 and 7900HT Fast Real-Time PCR systems.

Nucleotide. As used herein, "nucleotide" refers to a base-sugar-phosphate combination. A "nucleoside" refers to a base-sugar combination. Nucleotides are monomeric units of a nucleic acid sequence (e.g., DNA and RNA). The term nucleotide includes mono-, di- and triphosphate forms of deoxyribonucleosides and ribonucleosides and their derivatives. The term nucleotide particularly includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Examples of nucleotides suitable for use in the present compositions include, but are not limited to, dUTP, dATP, dTTP, dCTP, dGTP, dITP, 7-deaza-dGTP, a-thio-dATP, a-thio-dTTP, a-thio-dGTP, a-thio-dCTP or derivatives thereof, all of which are available commercially from sources including Life Technologies (Carlsbad, Calif.), New England BioLabs (Beverly, Mass.) and Sigma Chemical Company (Saint Louis, Mo.). Such dNTPs may be unlabeled, or they may be detectably labeled by coupling them by methods known in the art with radioisotopes (e.g., H3, C14, P32 or S35), vitamins (e.g., biotin), fluorescent moieties (e.g., fluorescein, rhodamine, Texas Red, or phycoerythrin), chemiluminescent labels, dioxigenin and the like. Labeled dNTPs may also be obtained commercially, for example from Life Technologies (Carlsbad, Calif.) or Sigma Chemical Company (Saint Louis, Mo.). In some embodiments of the present compositions, dNTPs can be added to give a final concentration in a working solution of each dNTP of about 0.001 to about 100 millimolar, about 0.01 to about 10 millimolar, about 0.1 to about 1 millimolar, or preferably about 0.2 to about 0.6 millimolar.

Polynucleotide and Oligonucleotide. As used herein, "polynucleotide" and "oligonucleotide" refer to a synthetic or biologically produced molecule comprising a covalently linked sequence of nucleotides which may be joined by a phosphodiester bond between the 3' position of the pentose of one nucleotide and the 5' position of the pentose of the adjacent nucleotide. In addition, a polynucleotide or oligonucleotide may contain modified or non-naturally occurring sugar residues (e.g., arabinose) and/or modified base residues. A polynucleotide or oligonucleotide may also comprise blocking groups that prevent the interaction of the molecule with particular proteins, enzymes or substrates.

Nucleic Acid. As used herein, "nucleic acid" includes compounds having a plurality of natural nucleotides and/or non-natural (or "derivative") nucleotide units. A "nucleic acid" can further comprise non-nucleotide units, for example peptides. "Nucleic acid" therefore encompasses compounds such as DNA, RNA, peptide nucleic acids, phosphothioate-containing nucleic acids, phosphonate-containing nucleic acids and the like. There is no particular limit as to the number of units in a nucleic acid, provided that the nucleic acid contains 2 more nucleotides, nucleotide derivatives, or combinations thereof, specifically 5, 10, 15, 25, 50, 100, or more. Nucleic acids can encompass both single and double-stranded forms, and fully or partially duplex hybrids (e.g., RNA-DNA, RNA-PNA, or DNA-PNA).

Primer. The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification. A primer is typically 11 bases or longer; more specifically, a primer is 17 bases or longer, although shorter or longer primers may be used depending on the need. As will be appreciated by those skilled in the art, the oligonucleotides may be used as one or more primers in various extension, synthesis or amplification reactions.

The complement of a nucleic acid sequence as used herein refers to a oligonucleotide or a polynucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature ("Tm") The Tm of a particular nucleic acid duplex under specified conditions is the temperature at which half of the base pairs have disassociated.

As used herein, "nucleic acid sample" refers to a sample used to test for presence or absence of a nucleic acid. The nucleic acid sample can be obtained from any source. Sources for nucleic acid samples include, but are not limited to, for example clothing, soil, skin, hair, blood, serum, feces, milk, saliva, urine, and/or other secretory fluids.

When referring to a thermostable DNA polymerase, one unit of activity is the amount of enzyme that will incorporate 10 nanomoles of dNTPs into acid-insoluble material (i.e., DNA or RNA) in 30 minutes under standard primed DNA synthesis conditions. "Working concentration" is used herein to mean the concentration of a reagent that is at or near the optimal concentration used in a solution to perform a particular function (such as amplification, sequencing or digestion of nucleic acids). The terms "stable" and "stability" as used herein generally mean the retention by an enzyme of at least 70%, preferably at least 80%, and most preferably at least 90%, of the original enzymatic activity (in units) after the enzyme or composition containing the enzyme has been stored for at least four weeks at a temperature of about 20-25° C., a year at a temperature of about 4° C. or at least 2 years at a temperature of −20° C.

As used herein, the term "target", "target sequence" or "target nucleic acid sequence" refers to a region of a nucleic acid which is to be either amplified, detected, or both. The target sequence resides between the two primer sequences used for amplification.

The compositions can further comprise probes for the detection of target nucleic acids. Various probes are known in the art, for example (TaqMan® probes (see, e.g., U.S. Pat. No. 5,538,848) various stem-loop molecular beacons (see, e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (see, e.g., Solinas et al., 2001, Nucleic Acids Research 29:E96 and U.S. Pat. No. 6,589,743), bulge loop probes (see, e.g., U.S. Pat. No. 6,590,091), pseudo knot probes (see, e.g., U.S. Pat. No. 6,589,250), cyclicons (see, e.g., U.S. Pat. No. 6,383,752), MGB Eclipse™ probe (Epoch Biosciences), hairpin probes (see, e.g., U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc 14:11155-11161. Probes can comprise reporter dyes such as, for example, 6-carboxyfluorescein (6-FAM) or tetrachlorofluorescin (TET). Detector probes can also comprise quencher moieties such as tetramethylrhodamine (TAMRA), Black Hole Quenchers (Biosearch), Iowa Black (IDT), QSY quencher (Molecular Probes), and Dabsyl and Dabcel sulfonate/carboxylate Quenchers (Epoch). Probes can also comprise two probes, wherein for example a fluor is on one probe, and a quencher on the other, wherein hybridization of the two probes together on a target quenches the signal, or wherein hybridization on a target alters the signal signature via a change in fluorescence.

In some embodiments, the probes are designed according to the methods and principles described in, for example, U.S. Pat. No. 6,727,356. Some probes can be sequence-based, for example 5' nuclease probes and some, such as SYBR® Green can be non-sequence specific DNA-binding dyes. In some preferred embodiments, the detector probe is a TaqMan® probe (Applied Biosystems, Foster City, Calif.). It is to be understood that a wide variety of probes are known in the art that may be useful in the present invention, including those not specifically disclosed herein.

In some embodiments of the disclosed compositions, the final probe concentration in a working solution can range from about 5 nM to about 750 nM, such as about 10 nM to about 600 nM, about 25 nM to about 500 nM, about 50 nM to about 400 nM, about 75 nM to about 300 nM, or any number in between. In some exemplary embodiments, the concentration of the probe is between about 100 nM to about 250 nM.

The present reaction mixtures may comprise an additive capable of facilitating or enhancing amplification, reverse transcription, and/or a combination of both reactions (e.g., agents for facilitating/enhancing PCR). Additives may be organic or inorganic compounds. Suitable additives include polypeptides as well as nonpolypeptide additives. Such additives may include, for example, uracil DNA glycosylase (UDG), lectins, *E. coli* single-stranded binding (SSB) protein, tRNA, rRNA, 7-deaza-2'-deoxyguanosine (dC7GTP), sulfur-containing compounds, acetate-containing compounds, dimethylsulfoxide (DMSO), glycerol, formamide, betaine, tetramethylammonium chloride (TMAC), polyethylene glycol (PEG), various surfactants and/or detergents, including anionic, cationic, zwitterionic or nonionic detergents (e.g., TWEEN 20, NP-40, Triton X-100,), ectoine, sodium azide, kathon, and polyols, to name just a few. Those of ordinary skill in the art will be able to identify additional additives for use in accordance with the present compositions, methods and kits.

Exemplary nucleic acids include DNA and RNA. In one embodiment, the nucleic acid is an isolated and/or purified nucleic acid. An isolated or purified nucleic acid is substantially free of other components such as proteins, polysaccharides, or other cellular, bacterial, or viral components. In another embodiment, the nucleic acid is not isolated or purified. For example, the nucleic acid may be present in a complex mixture, such as a crude lysate or whole cell extract. In another embodiment, the nucleic acid may be in situ and exist within its normal cellular, bacterial, or viral environment.

The nucleic acid may be obtained from natural sources, such as a variety of cells, tissues, organs, or organisms (including viruses). The nucleic acid may be obtained from cells, tissues, organs, or organisms in different developmental stages. The nucleic acid may be obtained from viruses, prokaryotes, or eukaryotes. Suitable viruses include herpes virus, HIV, influenza virus, Epstein-Barr virus, hepatitis virus, polio virus, and viroids. Suitable prokaryotes include species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium*, and *Streptomyces*. Suitable eukaryotes include fungi (specifically yeasts), plants, protozoa and other parasites, and animals including invertebrates such as insects (specifically *Drosophila* spp.), nematodes (specifically *Caenorhabditis elegans*), and vertebrates such as reptiles, amphibians (specifically *Xenopus laevis*) birds (specifically chicken), fish (specifically *Danio rerio*), and mammals (specifically mouse and human). The nucleic acid may also be obtained from cancer cells and precancerous cells obtained from animals, including humans. The nucleic acid may also be obtained from cell culture lines, including transformed and non-transformed cell culture lines. Nucleic acid samples can be extracted from a variety of sources. These include, but are not limited to, for example clothing, soil, paper, metal surfaces, air, water, plant parts, as well as human and/or animal skin, hair, blood, serum, feces, milk, saliva, urine, and/or other secretory fluids.

Following amplification or synthesis, the amplified or synthesized nucleic acid fragments may be isolated for further use or characterization. This step is usually accomplished by separation of the amplified or synthesized nucleic acid fragments by size or by any physical or biochemical means including gel electrophoresis, capillary electrophoresis, chromatography (including sizing, affinity and immunochromatography), density gradient centrifugation and immunoadsorption. An exemplary method is separation of nucleic acid fragments by gel electrophoresis, which provides a rapid and highly reproducible means of sensitive separation of a multitude of nucleic acid fragments, and permits direct, simultaneous comparison of the fragments in several samples of nucleic acids.

In one embodiment, one or more of the amplified or synthesized nucleic acid fragments are removed from the gel which was used for identification (see above), according to standard techniques such as chemical extraction, electroelution, or physical excision. The isolated unique nucleic acid fragments may then be inserted into standard vectors, including expression vectors, suitable for transfection or transformation of a variety of prokaryotic (bacterial) or eukaryotic (yeast, plant or animal including human and other mammalian) cells. Alternatively, nucleic acids produced by the methods may be further characterized, for example by sequencing (i.e., determining the nucleotide sequence of the nucleic acid fragments), by methods described below and others that are standard in the art (see, e.g., U.S. Pat. Nos. 4,962,022 and 5,498,523, which are directed to methods of DNA sequencing). Classical sequencing methods may also be employed such as the Sanger chain termination method (Sanger, F., et al. Proc. Natl. Acad. Sci. USA 74: 5463-5467 (1977)) and the Maxam and Gilbert chemical cleavage method (Maxam, A. M. and Gilbert, W. Proc. Natl. Acad. Sci. USA 74: 560-564 (1977)).

In some embodiments, the compositions may comprise a DNA-dependent DNA polymerase, an enzyme for reverse transcription (RNA-dependent DNA polymerase), and/or a combination of both types of enzymes. In some embodiments, a combination of DNA dependent DNA polymerases and/or a combination of RNA-dependent DNA polymerase can be present in the compositions disclosed herein.

Suitable DNA polymerases for amplification and/or sequencing include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Pyrococcus* sp KOD2 (KOD) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *Mycobacterium* DNA polymerase (Mtb, Mlep), *E. coli* pol I DNA polymerase, Klenow fragment, T5 DNA polymerase, T7 DNA polymerase, and generally pol I type DNA polymerases; mutants, variants and derivatives thereof, and combinations of the foregoing.

Suitable nucleic acid polymerases may be mesophilic or thermophilic, and are preferably thermophilic and thermostable. As used herein, the term "thermostable nucleic acid polymerase" refers to an enzyme which is relatively stable to heat when compared, for example, to nucleotide polymerases from *E. coli* and which catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. A representative thermostable enzyme isolated from *Thermus aquaticus* (Taq) is described in U.S. Pat. No. 4,889,818 and a method for using it in conventional PCR is described in Saiki et al., 1988, Science 239:487.

Suitable mesophilic DNA polymerases include Pol I family of DNA polymerases (and their respective Klenow fragments) any of which may be isolated from organism such as *E. coli, H. influenzae, D. radiodurans, H. pylori, C. aurantiacus, R. prowazekii, T. pallidum, Synechocystis* sp., *B. subtilis, L. lactis, S. pneumoniae, M. tuberculosis, M. leprae, M. smegmatis*, Bacteriophage L5, phi-C31, T7, T3, T5, SP01, SP02, mitochondrial from *S. cerevisiae* MIP-1, and eukaryotic *C. elegans*, and *D. melanogaster* (Astatke, M. et al., 1998, *J. Mol. Biol.* 278, 147-165), pol III type DNA polymerase isolated from any sources, and mutants, derivatives or variants thereof, and the like. Preferred thermostable DNA polymerases that may be used in the methods and compositions include Taq, Tne, Tma, Pfu, KOD, Tfl, Tth, Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; 5,512,462; WO 92/06188; WO 92/06200; WO 96/10640; WO 97/09451; Barnes, W. M., Gene 112:29-35 (1992); Lawyer, F. C., et al., PCR Meth. Appl. 2:275-287 (1993); Flaman, J.-M., et al., Nucl. Acids Res. 22(15):3259-3260 (1994)). Exemplary thermostable polymerases include the AmpliTaq polymerases from Roche Molecular Diagnostics (Pleasanton, Calif.).

In certain embodiments, the nucleic acid polymerase has 5'3' exonuclease activity. As defined herein, "5'→3' nuclease activity" or "5' to 3' nuclease activity" refers to that activity of a template-specific nucleic acid polymerase including either a 5'→3' exonuclease activity traditionally associated with some DNA polymerases whereby nucleotides are removed from the 5' end of an oligonucleotide in a sequential manner, (i.e., *E. coli* DNA polymerase I has this activity whereas the Klenow fragment does not), or a 5'→3' endonuclease activity wherein cleavage occurs more than one phosphodiester bond (nucleotide) from the 5' end, or both. Taq DNA polymerase has a DNA synthesis-dependent, strand replacement 5'-3' exonuclease activity (see Gelfand, "Taq DNA Polymerase" in PCR Technology: Principles and Applications for DNA Amplification, Erlich, Ed., Stockton Press, N.Y. (1989), Chapter 2). In solution, there is little, if any, degradation of labeled oligonucleotides.

The enzymes having DNA polymerase activity may be obtained commercially, for example from Roche Molecular Diagnostics (Pleasanton, Calif.), Life Technologies Corp. (Carlsbad, Calif.), Perkin-Elmer (Branchburg, N.J.), New England BioLabs (Beverly, Mass.) or Boehringer Mannheim Biochemicals (Indianapolis, Ind.). Alternatively, polymerases may be isolated from their natural sources according to standard procedures for isolating and purifying natural proteins that are well-known to one of ordinary skill in the art (see, e.g., Houts, G. E., et al., *J. Virol.* 29:517 (1979)). In addition, such polymerases may be prepared by recombinant DNA techniques that are familiar to one of ordinary skill in the art (see, e.g., Kotewicz, M. L., et al., *Nucl. Acids Res.* 16:265 (1988); U.S. Pat. No. 5,244,797; WO 98/47912; Soltis, D. A., and Skalka, A. M., *Proc. Natl. Acad. Sci. USA* 85:3372-3376 (1988)).

Embodiments that allow for RT-PCR further comprise an enzyme that has reverse transcriptase activity. Suitable enzymes having reverse transcriptase activity can be, for example, retroviral reverse transcriptases such as Moloney Murine Leukemia Virus (M-MLV) reverse transcriptase, Rous Sarcoma Virus (RSV) reverse transcriptase, Human Immunodeficiency Virus (HIV) reverse transcriptase, AMV reverse transcriptase, RAV reverse transcriptase, MAV reverse transcriptase, ASLV reverse transcriptases, as well as Lentivirus reverse transcriptases, or corresponding mutants, variants or derivatives thereof having reverse transcriptase activity. As used herein, "mutants, variants, or derivatives" refer to all permutations of a chemical species, which may exist or be produced, that still retains the definitive chemical activity of that chemical species. Some preferred enzymes for use in the invention include those that are RNase H+ enzymes such as, for example, RNase H+ M-MLV or RNase H+ AMV reverse transcriptases. Alternatively, the reverse transcriptases may have reduced, substantially reduced, or eliminated RNase H activity (see, e.g., U.S. Pat. No. 7,078,208, the disclosure of which is fully incorporated by reference in its entirety). RNase H is a processive 5' and 3' ribonuclease that is specific for the RNA strand of RNA-DNA hybrids (Perbal, A Practical Guide to Molecular Cloning, New York: Wiley & Sons (1984)). RNase H activity may be determined by a variety of assays, such as those described, for example, in U.S. Pat. No. 5,244,797, in Kotewicz, M. L., et al., Nucl. Acids Res. 16:265 (1988) and in Gerard, G. F., et al., FOCUS 14(5):91 (1992).

The reverse transcriptase may comprise a mutation as compared to the naturally-occurring reverse transcriptase. For example, the reverse transcriptase may be modified to contain a mutation that provides increased reverse transcriptase stability and/or functionality. Suitable enzymes may also include those in which terminal deoxynucleotidyl transferase (TdT) activity has been reduced, substantially reduced, or eliminated. Reverse transcriptases which exhibit such increased or decreased functionalities are described in, for example, U.S. Pat. Nos. 7,056,716 and 7,078,208 (the disclosures of which are fully incorporated by reference in their entireties).

In some embodiments, the reaction mixtures further comprise at least one PCR inhibitor blocking agent that assists in overcoming the inhibition of PCR reactions by a variety of inhibitor compounds often found in samples used for nucleic acid preparation and/or isolation. Such inhibitors include, for example, heparin (blood); hematin (blood); EDTA (blood); citrate (blood); immunoglobin G (blood, serum); humic acid (soil, feces); lactoferrin (milk, saliva, other secretory fluids); urea (urine); plant polysaccharides (plants); melanin (skin, hair); myoglobin (tissue); and indigo dye (textiles).

Suitable PCR inhibitor blocking agents include proteins such as, but not limited to, albumin (e.g. bovine serum albumin (BSA) and recombinant BSA)), gelatin (e.g., bovine gelatin and fish gelatin) and/or peptide or polypeptide variants, fragments or derivatives thereof. Exemplary proteins for use as PCR inhibitor blocking agents include bovine serum albumin (BSA) and fish gelatin. The PCR inhibitor blocking agent may comprise a combination of PCR inhibitor blocking agents. An exemplary combination of PCR inhibitor blocking agents is BSA and fish gelatin.

We have found that BSA and fish gelatin, both individually and in combination, is effective at reducing PCR inhibition by at least humic acid, hematin, and/or heparin. In some embodiments, this reduction of PCR inhibition is demonstrated by lower Ct values. As used herein the term "Ct" or "Ct value" refers to threshold cycle and signifies the cycle of a PCR amplification assay in which signal from a reporter that is indicative of amplicon generation (e.g., fluorescence) first becomes detectable above a background level. In some embodiments, the threshold cycle or "Ct" is the cycle number at which PCR amplification becomes exponential. In one embodiment, the signal from a reporter, such as fluorescence, is described as delta Rn. As used herein, the term "dRn" or "delta Rn" refers to the difference in the normalized reporter signal (Rn) subtracted from the background signal (baseline) which is then normalized by a passive reference signal. Delta Rn can be determined by the formula $Rn^+-Rn^-$, where $Rn^+$ is the Rn value for a reaction involving all components, including the template, and $Rn^-$ is the value for an unreacted sample.

According to various embodiments, a Ct value may be determined using a derivative of a PCR curve. For example, a first, second, or nth order derivative method may be performed on a PCR curve in order to determine a Ct value. In various embodiments, a characteristic of a derivative may be used in the determination of a Ct value. Such characteristics may include, but are not limited by, a positive inflection of a second derivative, a negative inflection of a second derivative, a zero crossing of the second derivative, or a positive inflection of a first derivative. In various embodiments, a Ct value may be determined using a thresholding and baselining method. For example, an upper bound to an exponential phase of a PCR curve may be established using a derivative method, while a baseline for a PCR curve may be determined to establish a lower bound to an exponential phase of a PCR curve. From the upper and lower bound of a PCR curve, a threshold value may be established from which a Ct value is determined. Other methods for the determination of a Ct value known in the art, for example, but not limited by, various embodiments of a fit point method, and various embodiments of a sigmoidal method (See, e.g., U.S. Pat. Nos. 6,303,305; 6,503,720; 6,783,934, 7,228,237 and U.S. Application No. 2004/0096819; the disclosures of which are herein incorporated by reference in their entireties).

Moreover, we have found that the higher the concentration of BSA used, the more tolerant the reaction is to hematin and humic acid inhibition. However, with increasing amounts of BSA, we also determined that dRn decreases and baseline value (or background signal) increases. As used herein, the term "dRn" or "delta Rn" refers to the difference in the normalized reporter signal (Rn) subtracted from the background signal (baseline) which is then normalized by a passive reference signal. Delta Rn can be determined by the formula $Rn^+-Rn^-$, where $Rn^+$ is the Rn value for a reaction involving all components, including the template, and $Rn^-$ is the value for an unreacted sample.

Surprisingly, we observed that by using such PCR inhibitor blocking agents in combination, such as fish gelatin and BSA, the level of inhibitor tolerance is greatly enhanced. Thus, the addition of PCR inhibitor blocking agents, including but not limited to fish gelatin and BSA, or combinations thereof, are effective in alleviating inhibition of a variety of PCR inhibitors typically found in samples used for nucleic acid analysis.

PCR inhibitor blocking compounds or agents can be added to the present compositions to give a final concentration in a working solution of about 0.05 mg/mL to about 0.8 mg/mL, about 0.1 mg/mL to about 0.6 mg/mL, and more specifically about 0.2 mg/mL to about 0.4 mg/mL. PCR inhibitor blocking agents may also be added as a percentage of the final concentration, for example, from about 0.05% (w/v) to about 0.8% (w/v), about 0.2% (w/v) to about 0.4% (w/v), and more specifically about 0.2% (w/v) to about 0.4% (w/v).

In some aspects, PCR inhibitor blocking agents can reduce the amount of PCR inhibition by such PCR inhibitors by at least 1 to 100% compared to the level of inhibition observed in the absence of such PCR inhibitor blocking agents. For example, inhibition can be reduced by at least about 1%, about 2%, about 5%, about 10%, about 20%, about 50%, about 75%, about 100% or any percentage in between.

Further we have found that the present composition decreases the overall run time of a PCR. For example, the overall PCR run time can be reduced by at least about 5%, about 10%, about 20%, about 50%, about 75%, about 100% or any percentage in between as compared to an equivalent PCR with a commercially available master mix.

Undesired amplification reactions, which can occur during the PCR process, usually begin during assembly of the reaction mixtures, or while the thermal cycler is heating to the initial denaturation temperature. These spurious reactions can be minimized by performing "hotstart" amplification. In general, hotstart techniques limit the availability of an essential reaction component until an elevated temperature, often >60° C., is reached. Several methods exist for performing hotstart including manual techniques, barriers, reversible polymerase inactivation, and specially-designed hairpin primers Manual hotstart methods require the researcher to withhold a critical component, usually magnesium or the polymerase, until the reaction has been heated. The withheld component then is added to initiate the reaction. A second method uses a physical barrier (e.g., wax) to separate a critical component from the template and primers. U.S. Pat. No. 5,565,339 describes using a wax barrier to separate the various PCR reagents from each other in a test tube. U.S. Pat. No. 5,413,924 describes using a paraffin wax bead to sequester the DNA polymerase.

A third method of hotstart amplification is reversible polymerase inactivation. The polymerase is reacted with an antibody or an oligonucleotide aptamer that binds to the polymerase's nucleotide binding domain, rendering the polymerase inactive. For example, a monoclonal antibody to Taq polymerase, such as the anti-Taq DNA polymerase antibody available from Sigma, is introduced into the reaction mixture. Upon heating, the compound dissociates from the polymerase, restoring enzyme activity. In another example, U.S. Pat. No. 5,677,152 describes a method in which the DNA polymerase is chemically modified to ensure that it only becomes active at elevated temperatures.

Another approach to achieve hotstart amplification is to design primers that will self-anneal to form specific hairpin structures. The hairpin primers will not be able to anneal to the target nucleic acid while in the hairpin conformation. The hairpin primers will remain in a hairpin conformation until heated to a denaturation temperature. However, if the hairpin structure includes a single-strand extension, then the hairpin structure itself resembles a primer annealed to a template and can result in strand extension.

As used herein the terms "annealing" and "hybridization" are used interchangeably and mean the complementary base-pairing interaction of one nucleic acid with another nucleic acid that results in formation of a duplex, triplex, or other higher-ordered structure. In some embodiments, the primary interaction is base specific, e.g., NT and G/C, by Watson/Crick and Hoogsteen-type hydrogen bonding. In some embodiments, base-stacking and hydrophobic interactions may also contribute to duplex stability. Conditions for hybridizing nucleic acid probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the probes and the complementary target sequences, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. Further, in general probes and primers of the present teachings are designed to be complementary to a target sequence, such that hybridization of the target and the probes or primers occurs. It will be appreciated, however, that this complementarity need not be perfect; there can be any number of base pair mismatches that will interfere with hybridization between the target sequence and the single stranded nucleic acids of the present teachings. However, if the number of base pair mismatches is so great that no hybridization can occur under even the least stringent of hybridization conditions, the sequence is not a complementary target sequence. Thus, by "substantially complementary" herein is meant that the probes or primers are sufficiently complementary to the target sequence to hybridize under the selected reaction conditions.

The term "label" as used herein refers to any atom or molecule which can be used to provide a detectable signal, and which can be attached to a nucleic acid or protein. Labels may provide signals detectable by fluorescence, radioactivity, colorimetry, gravimetry, X-ray diffraction or absorption, magnetism, enzymatic activity, and the like. In some embodiments, the detectable signal is a quantifiable signal.

For example, a label can be any moiety that: (i) provides a detectable signal; (ii) interacts with a second label to modify the detectable signal provided by the first or second label; or (iii) confers a capture function, e.g. hydrophobic affinity, antibody/antigen, ionic complexation. The skilled artisan will appreciate that many different species of reporter labels can be used in the present teachings, either individually or in combination with one or more different labels. Exemplary labels include, but are not limited to, fluorophores, radioisotopes, Quantum Dots, chromogens, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.5Ph.NCS," "Cy.7.0phEt.NCS," "Cy7.OphEt.CO2Su", and IRD800 (see, e.g., J. Flanagan et al., Bioconjug. Chem. 8:751-56 (1997); and DNA Synthesis with IRD800 Phosphoramidite, LI-COR Bulletin #111, LI-COR, Inc., Lincoln, Nebr.), electrochemiluminescence labels, including but not limited to, tris(bipyridal) ruthenium (II), also known as Ru(bpy)32+, Os(1,10-phenanthroline)2bis(diphenylphosphino)ethane2+, also known as Os(phen)2(dppene)2+, luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as Ru(v-bpy32+), and the like.

Fluorescent reporter molecule—quencher molecule pairs have been incorporated onto oligonucleotide probes in order to monitor biological events based on the fluorescent reporter molecule and quencher molecule being separated or brought within a minimum quenching distance of each other. For example, probes have been developed where the intensity of the reporter molecule fluorescence increases due to the separation of the reporter molecule from the quencher molecule. Probes have also been developed which lose their fluorescence because the quencher molecule is brought into proximity with the reporter molecule. These reporter-quencher molecule pair probes have been used to monitor hybridization assays and nucleic acid amplification reactions, especially polymerase chain reactions (PCR), by monitoring either the appearance or disappearance of the fluorescence signal generated by the reporter molecule. (For example, see U.S. Pat. No. 6,030,787).

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl) maleimide; benzoxadiazoles, stilbenes, pyrenes, and the like.

Preferably, reporter and quencher molecules are selected from fluorescein and rhodamine dyes. These dyes and appropriate linking methodologies for attachment to oligonucleotides are described in many references, e.g., Khanna et al. (cited above); Marshall, Histochemical J., 7: 299-303 (1975); Menchen et al., U.S. Pat. No. 5,188,934; Menchen et al., European Patent Application 87310256.0; and Bergot et al., International Application PCT/US90/05565.

In another embodiment, the reaction mixture may be present in a kit for use in the amplification of a nucleic acid molecule. Kits according to this embodiment comprise a carrier, such as a box, carton, tube or the like, having in close confinement therein, a container, such as a vial, tube, ampule, plate, bottle and the like. When more than one DNA polymerase is included in a kit (for example, a DNA polymerase and a reverse transcriptase), the polymerases may be in a single container as mixtures of two or more (e.g., 2, 3, 4, 5, etc), or in separate containers. The kits of the invention may also comprise (in the same or separate containers), a suitable buffer, a nucleotide, a PCR inhibitor blocking agent, a probes and/or a primer. In some embodiments, the DNA polymerase, PCR inhibitor blocking agent, nucleotide, and buffer are combined in a single tube or container.

In another aspect, the kits may comprise compositions for use in nucleic acid synthesis. Such compositions may be formulated as concentrated stock solutions (e.g., 2×, 3×, 4×, 5×, 6×, etc). In some embodiments, the compositions can be formulated as concentrated stock solutions in a single tube or container, comprising a DNA polymerase. In some preferred embodiments, such concentrated stock compositions may further comprise a PCR inhibitor blocking agent, a nucleotide, a hot start component, and/or a passive reference dye in a buffered solution. In some additional embodiments, such buffer solutions may comprise glycerol, DMSO, $Mg^{2+}$, and/or a detergent (such as TWEEN 20 or NP-40).

The following non-limiting examples further illustrate the various embodiments described herein.

EXAMPLES

Example 1

Exemplary Composition

An exemplary composition was formulated as a twofold concentrated stock solution comprising a thermostable DNA polymerase, a combination of PCR inhibitor blocking agents comprising BSA and fish gelatin, a buffered salt solution, a hot start component, dNTPs, glycerol, a nonionic detergent, and a passive reference dye. The exemplary PCR composition was tested in a number of assays as described in the Examples below.

Example 2

Superior Sensitivity, Accuracy, Dynamic Range, and Specificity of PCR with the Exemplary Composition The performance of the PCR composition of Example 1 in a panel of 13 TAQMAN® Gene Expression PCR assays was compared with the performance of a commercially available composition, TAQMAN® Universal PCR Master Mix (MM; Life Technologies, Inc.). Assays were performed according to the manufacturer's protocols for the assay and MM, but substituting the exemplary composition for MM in one set of assays.

A single assembled 20 μL PCR contains the following components:
Forward PCR primer (18 μM)
Reverse PCR primer (18 μM)
TAQMAN® probe (5 μM)
nucleic acid sample (10 to 100 ng)
TAQMAN® Universal PCR Master Mix or the composition of Example 1 (10 μL), RNase-free water to total PCR volume of 20 μL For each of the 13 TAQMAN® Gene Expression PCR assays tested, the Forward PCR primer, Reverse PCR primer, and TAQMAN® probe were components of a TAQMAN® Gene Expression Assay Mix (20×).

Thermal cycling conditions for PCR amplification of the assay panel were selected in accordance with the following:
UNG Step (Optional): 50° C., 2 minutes
Activation: 95° C., 20 seconds
(Denaturation: 95-97° C./1-3 seconds;
Extension: 60-62° C./20-30 seconds)×40 cycles Threshold cycle numbers (Ct) determined for each assay on standard PCR instrumentation using the composition of Example 1 or the commercial MM are shown in FIG. 1. Smaller Ct values were determined using the exemplary composition than with the commercial concentrate for most of the assays, demonstrating that the claimed composition is more sensitive than the commercially available concentrate.

Figure 2:
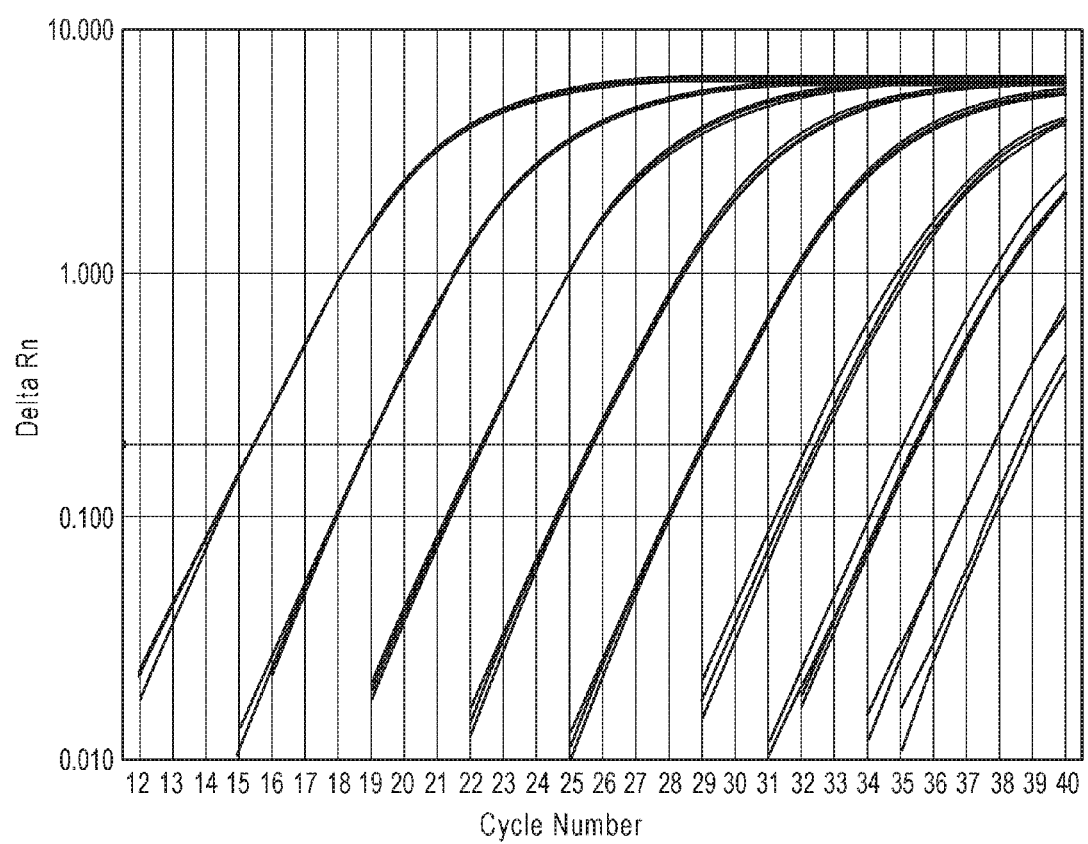
FIG. 2 shows representative amplification plots from real-time PCR for a dilution series of human cDNA amplified in 4 replicate reactions using an embodiment of the compositions disclosed herein at a 2× concentration in the FN1 TAQMAN® Gene Expression assay on an Applied Biosystems 7500 Fast Real-time PCR System.

The large dynamic range of PCR assays performed using the exemplary composition is shown in FIG. 2, which presents representative amplification plots from real-time PCR for a dilution series of human cDNA amplified in 4 replicate reactions using an embodiment of the claimed reagent twofold concentrate in the FN1 TAQMAN® Gene Expression assay on an Applied Biosystems 7500 Fast Real-time PCR System.

The dynamic range of the exemplary composition in a panel of TAQMAN® Gene Expression assays was compared to that of several commercially available reagent mixes, using the respective recommended protocols and a nucleic acid sample. The results of this comparison are shown in Table 2 below. In Table 2, the log of the limit of detection (LOD) is shown for each reagent mixture. Logs detected have PCR efficiency between 85-115% and R2 values>0.98. Six replicate reactions were run with each reagent mixture on an Applied Biosystems 7900HT Fast Real-time PCR System.

TABLE 2

Assay dynamic range compared between exemplary composition and commercially available reagent mixtures.

| ASSAY | ASSAY TYPE | TAQMAN® FAST ADVANCED MASTER MIX | ROCHE FASTSTART® REAGENT | QIAGEN QUANTITECT® REAGENT | QIAGEN QUANTIFAST® REAGENT | BIO-RAD ITAQ™ SUPERMIX | BIO-RAD ITAQ™ FAST SUPERMIX |
|---|---|---|---|---|---|---|---|
| APOA1 | Good Fast | 7 | 5 | 5 | 5 | 5 | 5 |
| APOA1 (FAM™)/ GAPDH (VIC®) | Good Fast | 7 | 4 | 4 | 5 | 5 | 5 |
| APOA1 (FAM™)/ | Housekeeping | 7 | 7 | 7 | 7 | 7 | 7 |

TABLE 2-continued

Assay dynamic range compared between exemplary composition and commercially available reagent mixtures.

| ASSAY | ASSAY TYPE | TAQMAN ® FAST ADVANCED MASTER MIX | ROCHE FASTSTART ® REAGENT | QIAGEN QUANTITECT ® REAGENT | QIAGEN QUANTIFAST ® REAGENT | BIO-RAD ITAQ ™ SUPERMIX | BIO-RAD ITAQ ™ FAST SUPERMIX |
|---|---|---|---|---|---|---|---|
| GAPDH (VIC ®) | | | | | | | |
| UBC | Housekeeping | 6 | 4 | 4 | 5 | 5 | 5 |
| HIST1H3F | LenAmpLong | 5 | 3 | 3 | 3 | 3 | 3 |
| TXNDC | GCAmpLow, PrimerLong | 5 | 2 | 2 | 3 | 3 | 3 |
| FOXD1 | GCAmpHigh | 4 | 2 | 2 | 2 | 2 | 2 |
| GPR34 | GCProbeLow, LowdRn | 3 | 1 | 2 | 2 | 2 | 2 |
| WISP | HighProbeTm | 2 | 0 | 0 | 1 | 1 | 1 |

TABLE 2

| Logs | Final (ng/μL) |
|---|---|
| 7 | 0.00001 |
| 6 | 0.0001 |
| 5 | 0.001 |
| 4 | 0.01 |
| 3 | 0.1 |
| 2 | 1 |
| 1 | 10 |

The results in Table 2 show that the exemplary composition has a dynamic range for a variety of types of TAQMAN® Gene Expression assays that is larger than that of the commercially available reagent mixtures.

Example 3

Greater Tolerance of PCR Performed with the Disclosed Composition for PCR Inhibitors Experiments were performed to determine the robustness of the exemplary composition to presence of PCR inhibitors in assembled reactions. Hematin and heparin are two PCR inhibitors commonly contaminating nucleic acid samples from blood, while humic acid is a common PCR inhibitor contaminating nucleic acid samples from soil, plants, or feces.

Representative data are shown below for a single dilution (10 ng/reaction) of cDNA run as simplex FAM reactions or duplex reactions of FAM and an 18S (VIC) endogenous control for the following FAM TAQMAN® assays in the presence of hematin at concentrations from 10-50 μM following the manufacturer's protocol for TAQMAN® Universal Master Mix II (MMII), but substituting the exemplary composition for the MMII:

| Assay ID | Type |
|---|---|
| Hs00157812_m1 | Amp >70 C. |
| Hs00159092_m1 | Gene Family |
| Hs00162613_m1 | Gene Family |
| Hs00192202_m1 | Primer <16 nt |
| Hs00197394_m1 | Probe <30% GC |
| Hs00259126_m1 | Good Fast |
| Hs00261096_s1 | Amp <30% GC |
| Hs00298216_s1 | Amp <30% GC |

Results for the assays are shown in the FIGS. 7A-7D. Most of the assays were within 1 Ct of the control throughout the range tested (10 μM-50 μM), showing that PCR reactions assembled with the composition are tolerant of hematin concentrations in that range.

Tolerance for humic acid in PCR samples assembled with the composition was also tested. As little as 15 ng humic acid contaminating a PCR sample completely inhibits PCR.

Figure 8:
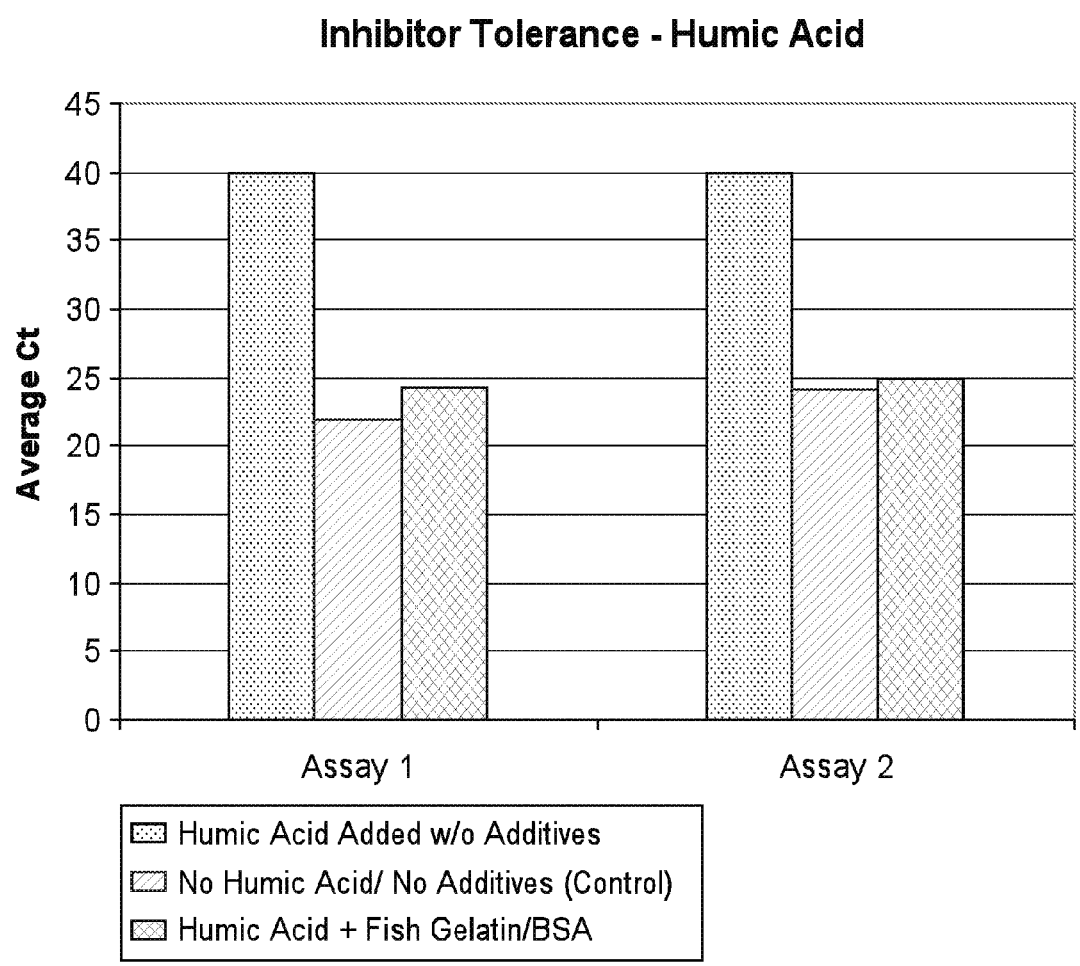
FIG. 8 presents a histograph showing average Ct measured for two TAQMAN® Gene Expression assays in the absence of humic acid or with humic acid present at 15 ng/20 μL reaction in the presence or absence of the additives, BSA and fish gelatin.

PCR experiments using two TAQMAN® Gene Expression assays in the absence of humic acid or with humic acid present at 15 ng/20 μL reaction in the presence or absence of the additives, BSA and fish gelatin, in the exemplary composition were performed. The results are summarized in the histogram of FIG. 8.

Inclusion of a combination of fish gelatin and BSA in the sample results in PCR amplification in the range of the control PCR. Thus, the exemplary composition is tolerant of up to 15 ng of humic acid in PCR samples.

Additionally, tolerance for heparin in PCR samples assembled with the composition was tested. As little as 0.01 U/μL heparin in a PCR sample completely inhibits the reaction.

Figure 9:
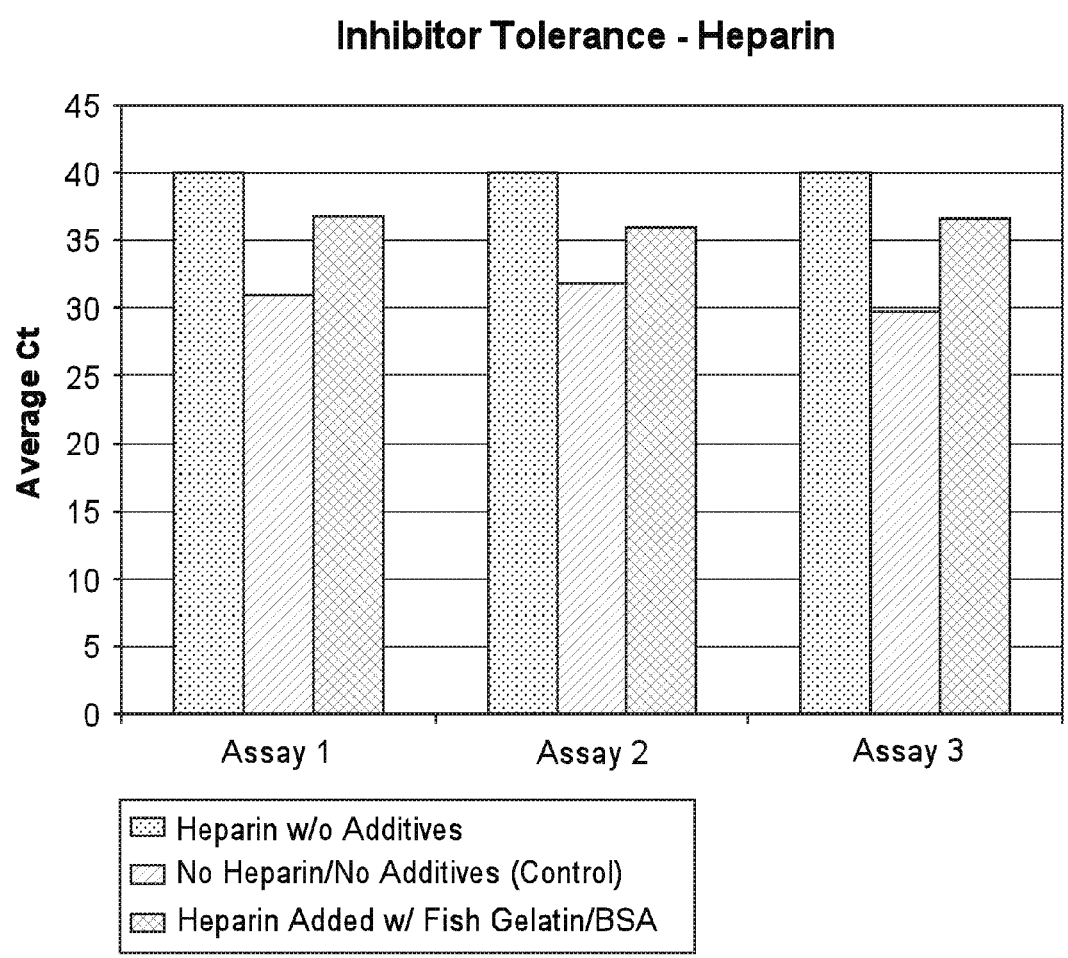
FIG. 9 presents a histograph showing average Ct measured for three TAQMAN® Gene Expression assays in the absence of heparin and with heparin present at 0.01 U/μL in the presence or absence of the additives, BSA and fish gelatin.

PCR experiments using three TAQMAN® Gene Expression assays in the absence of heparin or with 0.01 U/μL heparin present in the presence or absence of the additives, BSA and fish gelatin, in the exemplary composition were performed. The results are summarized in the histogram of FIG. 9.

Inclusion of a combination of fish gelatin and BSA in the sample results in PCR amplification in a detectable range. Thus, the exemplary composition is tolerant of up to 0.01 U/uL heparin in PCR samples.

Example 4

Enhanced Benchtop Stability of Reactions Assembled for PCR with the Disclosed Composition The composition of Example 1 was shown to produce assembled reactions with enhanced stability at room temperature. Representative results of amplification performed immediately after reaction assembly vs. amplification after incubating the assembled reaction at 30° C. for 72 hours are shown in FIGS. 3A-3B.

Figure 3A:
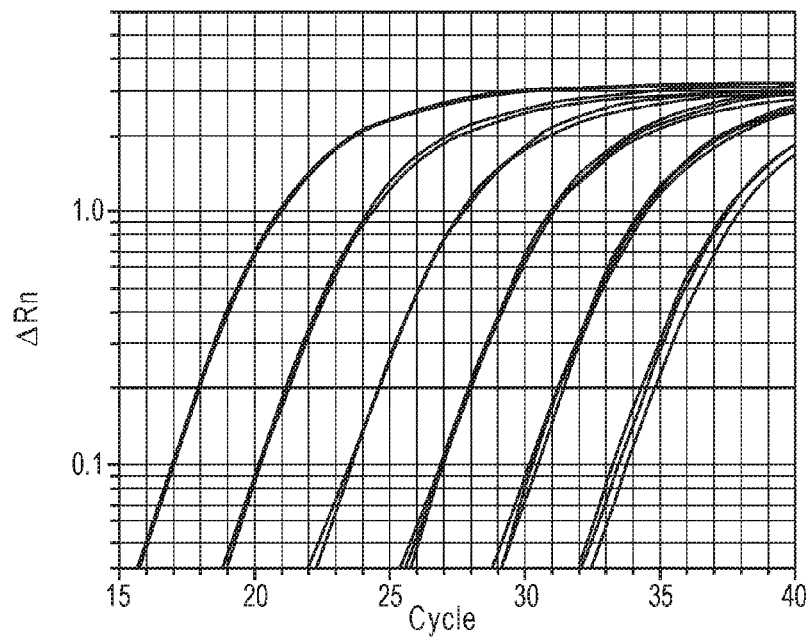
FIGS. 3A-B shows graphs of Δ Rn as a function of PCR cycle for a dilution series of human cDNA amplified in 4 replicate runs of the B2M TAQMAN® Gene Expression Assay using an embodiment of the compositions disclosed herein at a 2× concentration run upon assembly of the final reaction (FIG. 3A) and after 72 hours of incubation of the assembled final reaction at 30° C.
Figure 3B:
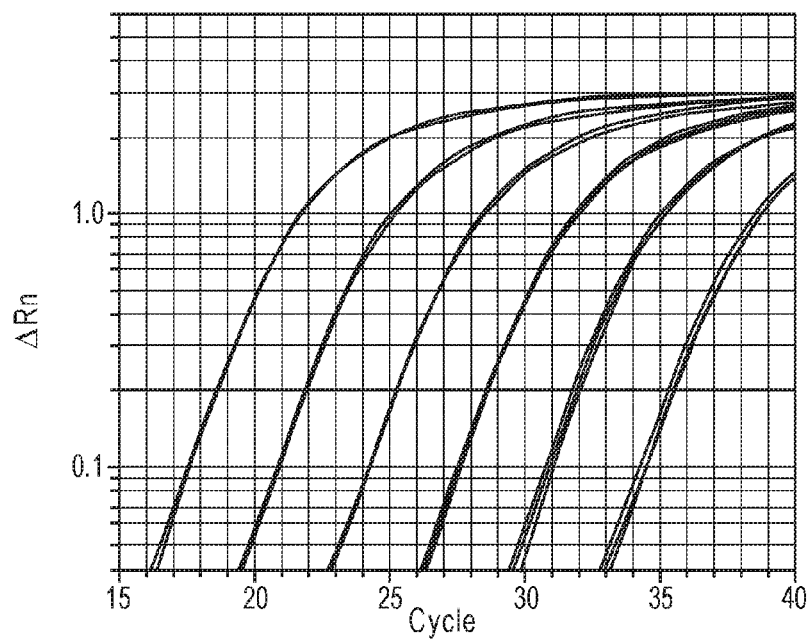

The amplification results shown in FIGS. 3A-3B are summarized quantitatively in Tables 3 and 4. Table 3 shows that PCR efficiency remains high after 72 hours at 30° C. with negligible impact on the R2. Table 4 shows that for each of the dilution levels, the CT determined at 72 hrs showed little increase over that determined immediately.

TABLE 3

| PCR efficiency and R2 at 0 or 72 hrs. | | | |
|---|---|---|---|
| PCR Efficiency | | $R^2$ | |
| 0 HR | 72 HR | 0 HR | 72 HR |
| 99.7% | 100.0% | 0.9998 | 0.9997 |

TABLE 4

| $C_t$ determined for each dilution at 0 hr or 72 hrs. | | |
|---|---|---|
| FINAL CONC. ng/ml | | $C_t$ |
| cDNA | 0 HR | 72 HR |
| 10 | 17.81 | 18.34 |
| 1 | 20.99 | 21.59 |
| 0.1 | 24.32 | 24.95 |
| 0.01 | 27.65 | 28.24 |
| 0.001 | 31.18 | 31.80 |
| 0.0001 | 34.34 | 34.80 |

Example 5

Figures 4A, 4B:
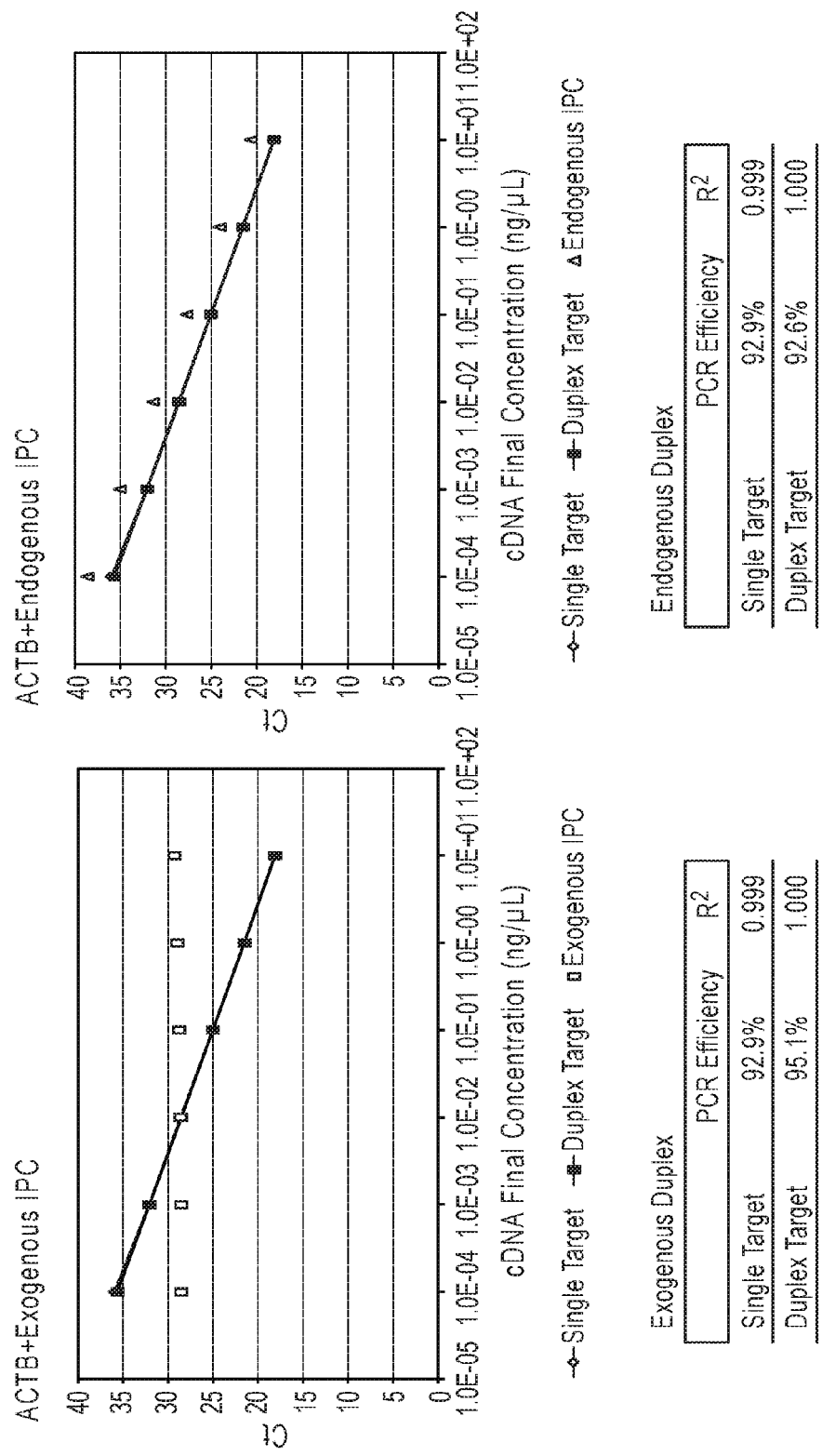
FIG. 4A shows a graph of Ct as a function of final concentration (ng/μL) cDNA comparing serial dilutions of single target (beta-actin gene (ACTB) or an exogenous internal positive control (IPC) target) PCR reaction TAQMAN® Gene Expression assays using an embodiment of the disclosed compositions at a 2× concentration with serial dilutions of duplex target (ACTB and IPC) PCR reaction TAQMAN® Gene Expression assays using an embodiment of the disclosed compositions at a 2× concentration.
FIG. 4B shows a graph of Ct as a function of final concentration (ng/μL) cDNA comparing serial dilutions of single target (beta-actin gene (ACTB) or an endogenous internal positive control (IPC) target) PCR reaction TAQMAN® Gene Expression assays using an embodiment of the disclosed compositions at a 2× concentration with serial dilutions of duplex target (ACTB and IPC) PCR reaction TAQMAN® Gene Expression assays using an embodiment of the claimed composition.

Comparison of PCR Performed with the Disclosed Composition for Single Target and Duplexed Targets Amplification using the composition of Example 1 was compared for single target PCR and duplexed PCR including the target and an internal positive control. The internal positive control (IPC) was either an exogenous IPC (KIT info here) or an endogenous IPC assay (GAPDH). The target was in the beta-actin gene (ACTB), which was serially diluted prior to amplification with a constant quantity of the exogenous (FIG. 4A) or endogenous (FIG. 4B) IPC assay. Results are shown in FIGS. 4A-4B.

Example 6

Reduced PCR Run Times on Standard or Fast Instrumentation

Figure 6:
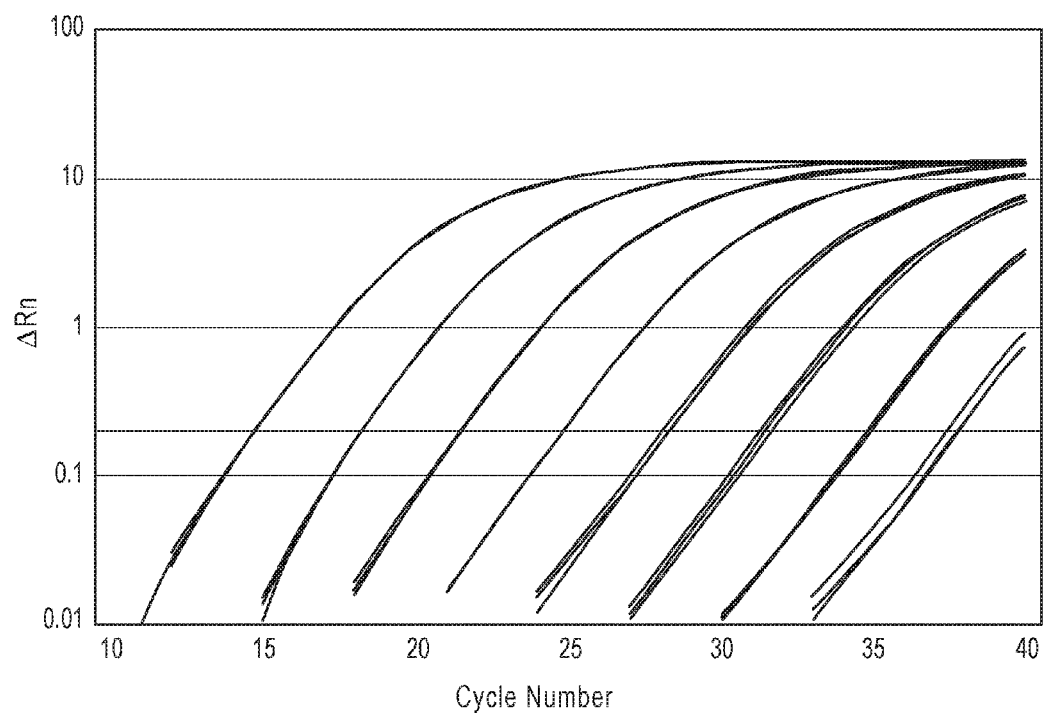
FIG. 6 presents a graph of ΔRn vs. PCR cycle for serial dilutions of human cDNA amplified in 4 replicate real-time PCR reactions for the FN1 TAQMAN® Gene Expression assay performed using an embodiment of the disclosed compositions at a 2× concentration on an Applied Biosystems 7300 Real-time PCR System.
Figure 7A:
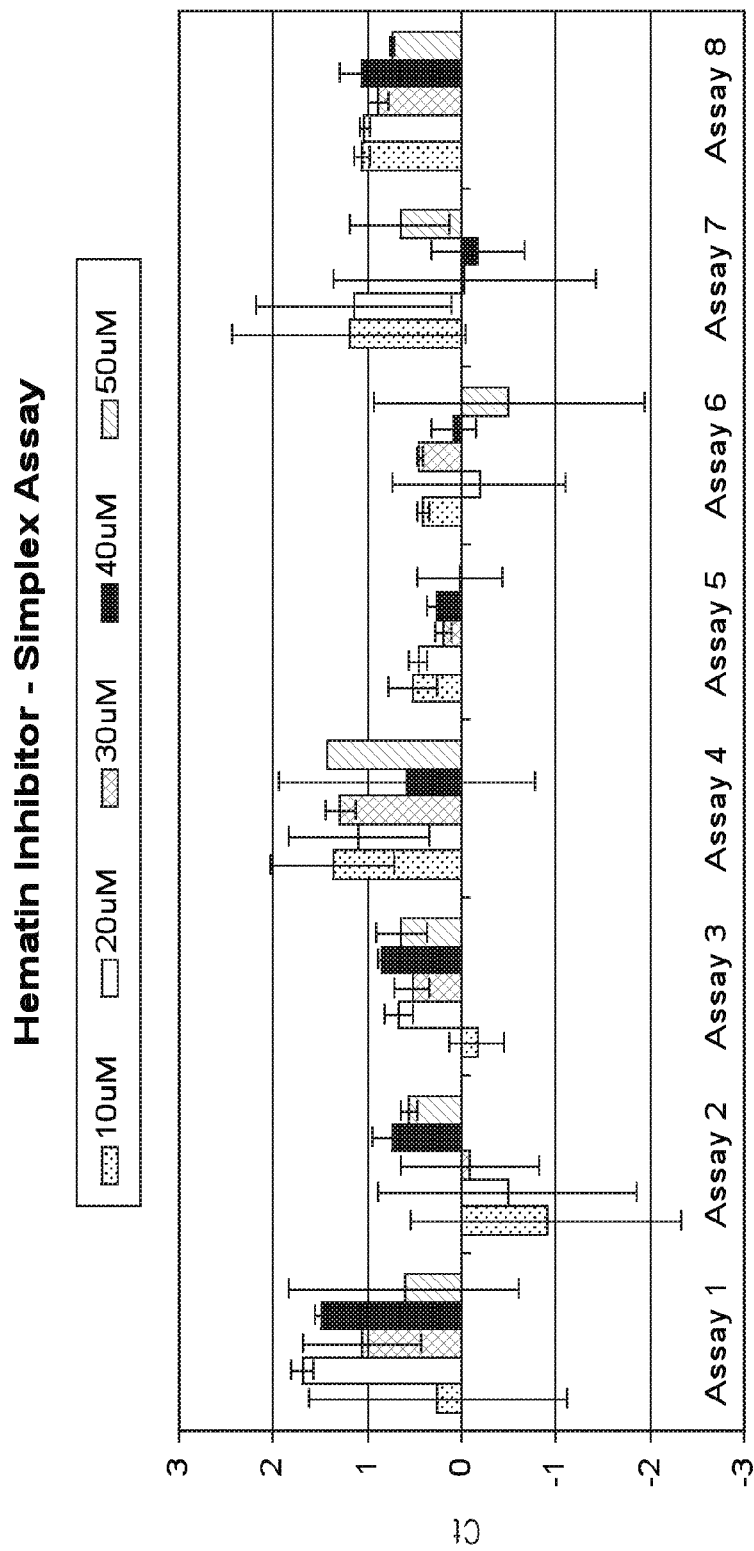
FIGS. 7A-7B presents histographs showing Ct measured for 8 simplex FIG. 7A or duplexed FIG. 7B TAQMAN® Gene Expression assays with hematin present at 10-50 μM.
Figure 7B:
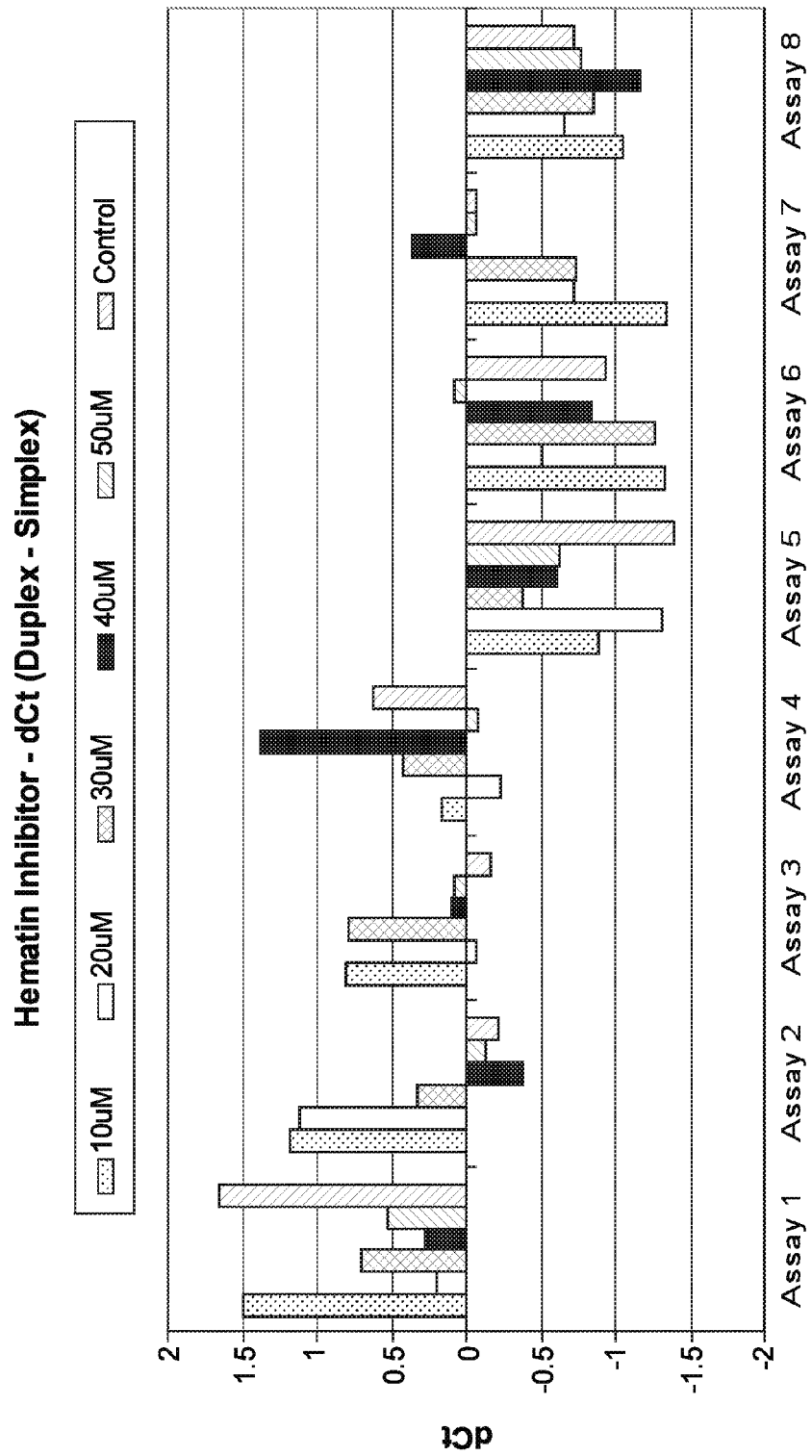
Figure 7C:
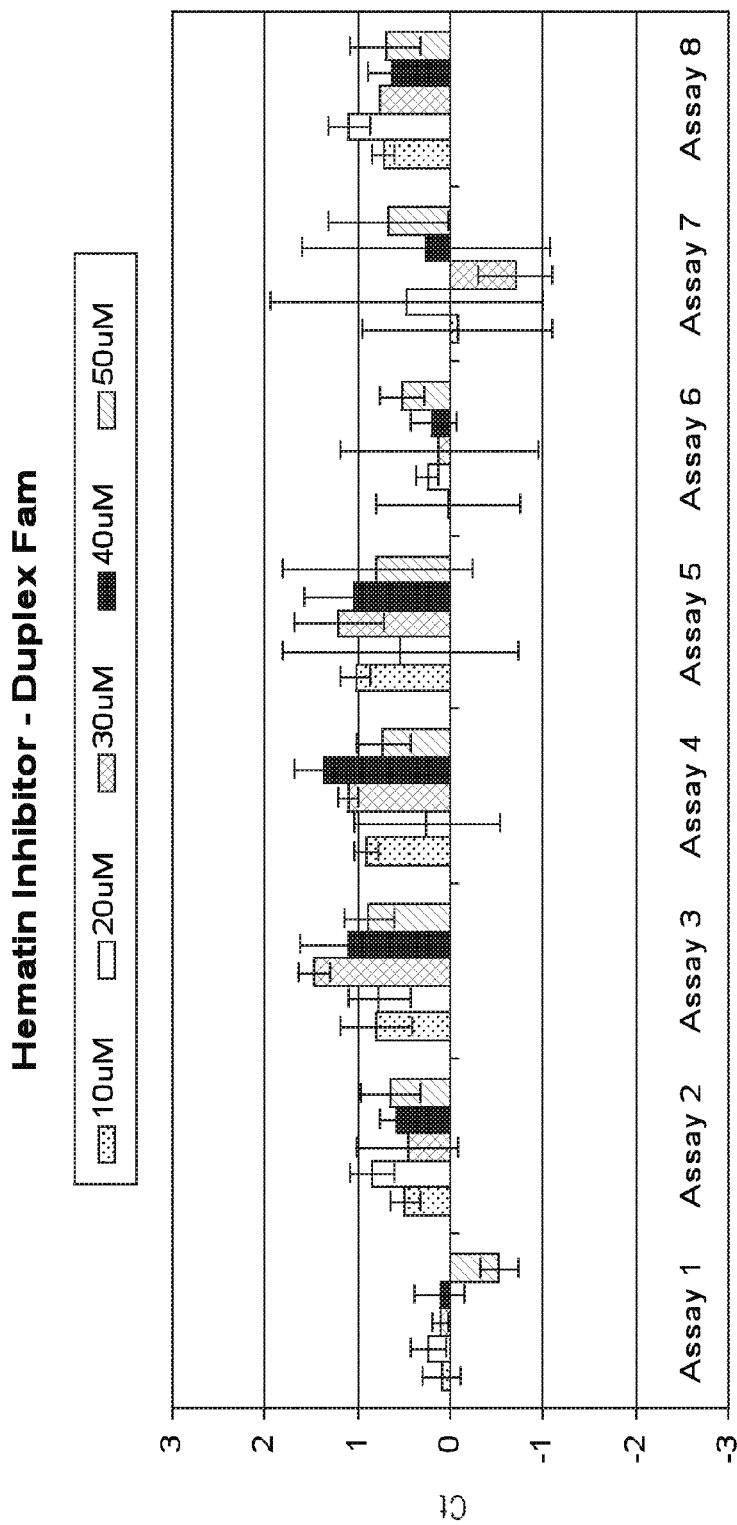
FIGS. 7C-7D presents histographs showing FIG. 7C dCt measured for the 8 simplex and duplexed TAQMAN® Gene Expression assays with hematin present at 10-50 μM and FIG. 7D Ct measured for 8 duplexed VIC control TAQMAN® Gene Expression assays with hematin present at 10-50 μM.
Figure 7D:
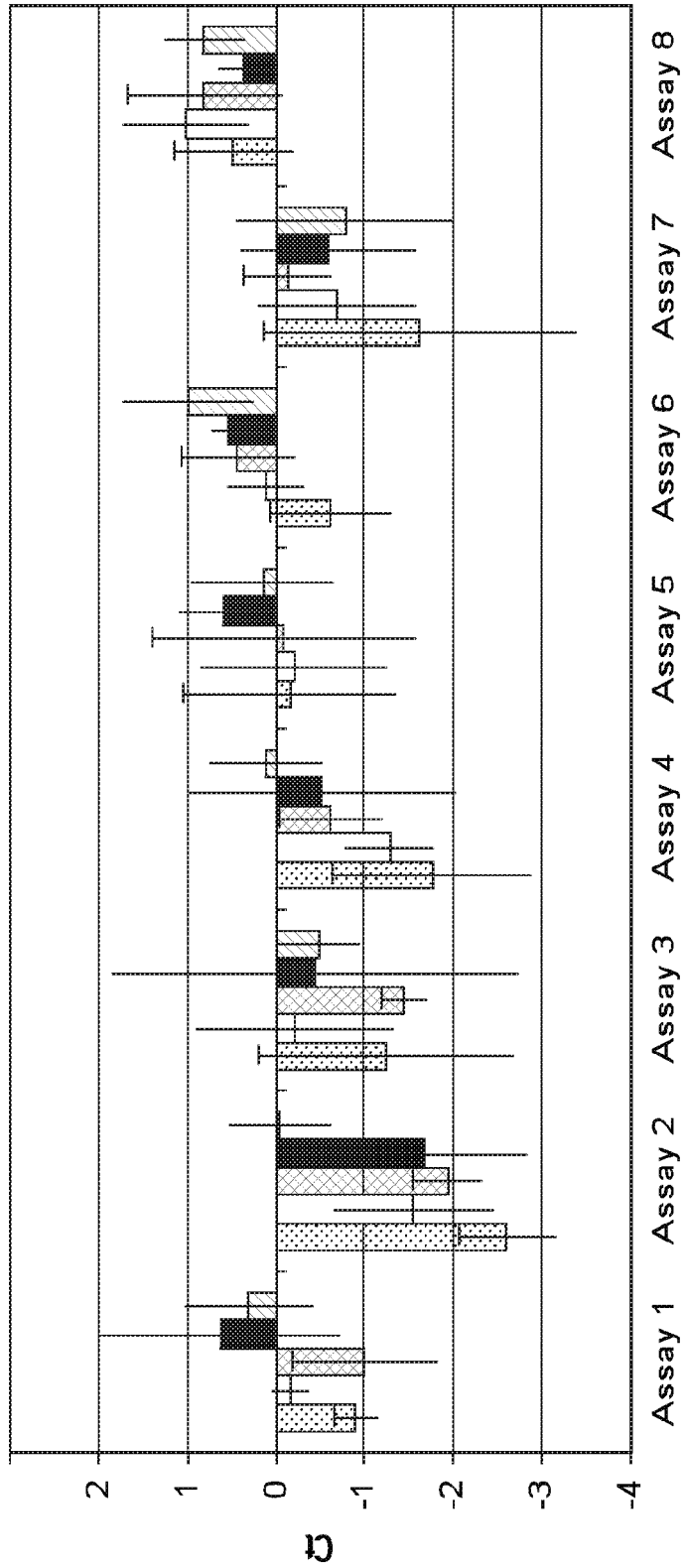

FIG. 6 shows the amplification results achieved on serial dilutions of human cDNA amplified in the FN1 TAQMAN® Gene Expression assay when using the composition of Example 1 under fast thermal cycling conditions on an Applied Biosystems 7300 real-time PCR system, an instrument for standard rather than fast real-time PCR. Thermal cycling time is significantly reduced.

Example 7

Application to miRNA Assays

The composition of Example 1 was shown to perform well in commercial assays for microRNA.

Figure 5A:
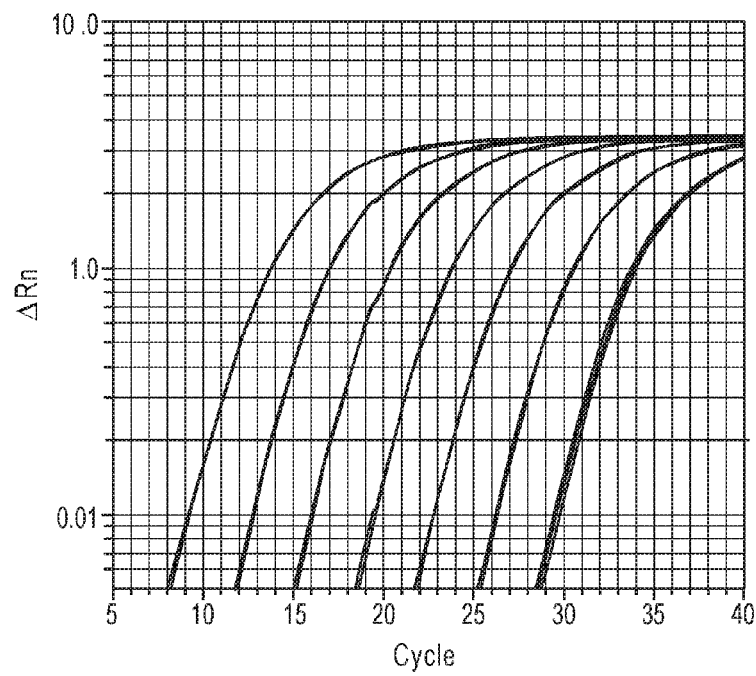
FIGS. 5A-5B presents an amplification plot FIG. 5A of ΔRn vs. PCR cycle and a standard curve FIG. 5B of Ct as a function of final nucleic acid concentration for real-time PCR of a dilution series of 4 replicate reactions for the Let7-c TAQMAN® MicroRNA assay performed using an embodiment of the disclosed compositions at a 2× concentration on an Applied Biosystems 7900H Fast Real-time PCR System.
Figure 5B:
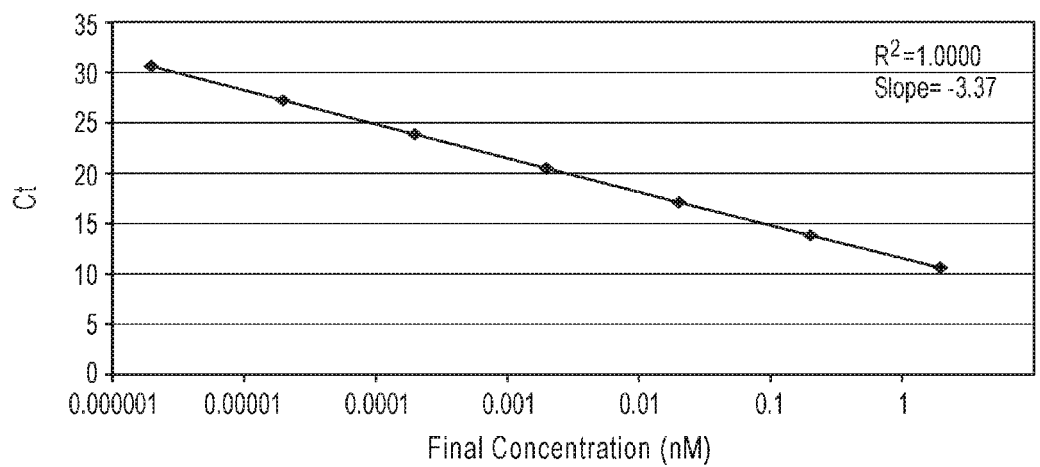

Results from a representative assay are shown in FIGS. 5A-5B. FIG. 5A presents an amplification plot showing ΔRn vs. PCR cycle while FIG. 5B presents a standard curve of Ct as a function of final nucleic acid concentration for real-time PCR of a dilution series of 4 replicate reactions for the Let7-c TAQMAN® MicroRNA assay performed using the composition of Example 1 on an Applied Biosystems 7900H Fast Real-time PCR System.

The standard curve in FIG. 5B shows excellent linearity of PCR amplification over a 6-log range of input template concentration.

As shown in FIGS. 10A-10B, the composition of Example 1 shows comparable results in simplex and duplex reactions under fast thermal cycling conditions. Further, the results in both simplex and duplex reactions is similar to the results obtained with the FN1 TAQMAN® Gene Expression assay.

The singular forms "a," "an," and "the" include plural referents unless the context clearly dictates otherwise. The term "about" before a quantitative amount indicates that acceptable possible variation from the amount is −+10% of the amount, unless specified otherwise. The endpoints of all ranges reciting the same characteristic or amount are independently combinable and inclusive of the recited endpoint. The terms "first," "second," and the like do not denote any order, quantity, or importance, but rather are used to distinguish one element from another. All references cited herein are incorporated herein by reference in their entirety.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All publications, patents, and patent applications mentioned in this specification are herein incorporated by reference to the same extent as if each individual publication, patent, or patent application was specifically and individually indicated to be incorporated by reference.

What is claimed is:

1. A polymerase chain reaction (PCR) composition, comprising:
    a thermostable DNA polymerase; and
    a combination of PCR inhibitor blocking agents comprising fish gelatin and bovine serum albumin (BSA), wherein the bovine serum albumin is at a concentration of 0.05 mg/mL to 0.8 mg/mL and wherein the fish gelatin is at a concentration of 0.05% (w/v) to 0.8% (w/v).

2. The composition of claim 1, further comprising a nonionic detergent.

3. The composition of claim 1, wherein the composition is stable at room temperature for up to 48 hours.

4. The composition of claim 3, wherein the composition is stable at room temperature for up to about 72 hours.

5. The composition of claim 1, wherein the concentration of the thermostable DNA polymerase is about 100 to about 500 units per milliliter.

6. The composition of claim 1, further comprising a reagent for hotstart PCR.

7. The composition of claim 6, wherein the reagent is an antibody, an aptamer, a hairpin primer, or a sequestration wax bead.

8. The composition of claim 1, further comprising one or more deoxynucleoside triphosphates.

9. The composition of claim 1, further comprising a passive reference control.

10. The composition of claim 1, wherein BSA is at a concentration of 0.05 mg/mL to 0.1 mg/mL, and fish gelatin is at a concentration of 0.2% (w/v) to 0.4% (w/v), or 0.2% (w/v) to 0.8% (w/v).

11. The composition of claim 1, wherein the concentration of bovine serum albumin is about 0.3 mg/mL and the concentration of fish gelatin is about 0.3% (w/v).

12. The composition of claim 1, wherein the BSA is at a concentration of 0.1 mg/mL to 0.6 mg/mL, or 0.2 mg/mL to 0.4 mg/mL, and the fish gelatin is at a concentration of 0.2% (w/v) to 0.4% (w/v), or 0.2% (w/v) to 0.8% (w/v).

13. A kit comprising the composition of claim 1, further comprising a control nucleic acid sample, and a primer pair specific for PCR amplification of a DNA target in the control nucleic acid sample.

14. A method for nucleic acid synthesis comprising:
adding the composition of claim 1 to a reaction vessel;
adding a nucleic acid sample and a primer to the reaction vessel; and
synthesizing a nucleic acid using the nucleic acid sample as a template.

15. A method for blocking inhibition of a polymerase chain reaction (PCR) or decreasing the run time of a PCR by PCR inhibitors, comprising:
adding the composition of claim 1 to a reaction vessel, wherein the composition blocks the inhibition of PCR by PCR inhibitors or decreases the run time of a PCR;
adding a nucleic acid sample and a primer to the reaction vessel; and
performing PCR on the nucleic acid sample.

16. The method of claim 15, wherein the PCR is a simplex PCR.

17. The method of claim 15, wherein the PCR is a multiplex PCR.

18. The method of claim 15, wherein the PCR inhibitor is hematin and wherein up to 50 µM hematin is tolerated in the PCR.

19. The method of claim 15, wherein the PCR inhibitor is humic acid and wherein up to 15 ng of humic acid per 20 µL reaction volume is tolerated in the PCR.

20. The method of claim 15, wherein the PCR inhibitor is heparin and wherein up to 0.01 U/µL heparin is tolerated in the PCR.

* * * * *